(12) United States Patent
Salehi et al.

(10) Patent No.: US 9,072,730 B2
(45) Date of Patent: Jul. 7, 2015

(54) METHOD OF IMPROVING COGNITIVE FUNCTIONS IN INDIVIDUALS WITH DOWN SYNDROME AND/OR ALZHEIMER'S DISEASE

(75) Inventors: Ahmad Salehi, Palo Alto, CA (US);
William C. Mobley, La Jolla, CA (US);
Janice Vallette, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 893 days.

(21) Appl. No.: 12/801,002

(22) Filed: May 14, 2010

(65) Prior Publication Data

US 2010/0298431 A1    Nov. 25, 2010

Related U.S. Application Data

(60) Provisional application No. 61/213,173, filed on May 14, 2009.

(51) Int. Cl.
| | | |
|---|---|---|
| *A61K 31/235* | (2006.01) | |
| *A61K 31/24* | (2006.01) | |
| *A61K 31/195* | (2006.01) | |
| *A61K 31/44* | (2006.01) | |

(52) U.S. Cl.
CPC ..................................... *A61K 31/44* (2013.01)

(58) Field of Classification Search
USPC .......................................... 514/567, 533, 538
See application file for complete search history.

(56) References Cited

U.S. PATENT DOCUMENTS

| 4,690,949 A | 9/1987 | Yoshida et al. |
|---|---|---|
| 5,304,367 A | 4/1994 | Biegon |
| 5,602,150 A | 2/1997 | Lidsky |
| 6,551,993 B1 | 4/2003 | Schneider |
| 2004/0180931 A1 | 9/2004 | Pratt |
| 2007/0071724 A1 | 3/2007 | Arancio et al. |
| 2008/0108568 A1 | 5/2008 | Stephan et al. |
| 2009/0023705 A1 * | 1/2009 | Roberts et al. ........... 514/211.13 |

FOREIGN PATENT DOCUMENTS

| EP | 1244 435 B1 * | 11/2007 | ............. A61K 31/00 |
|---|---|---|---|

OTHER PUBLICATIONS

Costa et al. in Neuropsychopharmacology (2008) 33, 1624-1632.*
Howells et al. in Brain Research 1200 (2008), 107-115.*
Ogawa et al. in Acta Medica Okayama (1984) 38(3), 301-304 (English Abstract provided).*
Tzavara et al. in Molecular Psychiatry (2006) 11, 187-195.*
Goldstein et al. in Cardiovascular Drug Reviews, vol. 24, No. 3-4, pp. 189-203.*
Boomsma et al. in Journal of Chromatography, 427 (1988) 219-227.*
Marsh et al. in Movement Disorders 24(2), 277-282 (2009).*
Kalinin et al. in Neurobiology of Aging 28 (2007) 1206-1214.*
Bywater et al. in Neuropsychopharmacology 2002 27(5) 699-711.*
Szapacs, et al. "late onset loss of hippocampus 5-HT and NE is accompanied by increases in BDNF protein expression in mice co-expressing mutant APP and PS1", Neurobiol. Dis. Aug. 16, 2004(3): 572-80 (Abstract attached).

* cited by examiner

*Primary Examiner* — James O Wilson
*Assistant Examiner* — Oluwafemi Masha
(74) *Attorney, Agent, or Firm* — William E. Beaumont

(57) ABSTRACT

A method of treating an individual having Down syndrome or Alzheimer's disease, which entails the step of administering an amount of one or more compounds to the individual which improve cognitive functioning in the individual by increasing hippocampal NE levels.

16 Claims, 21 Drawing Sheets

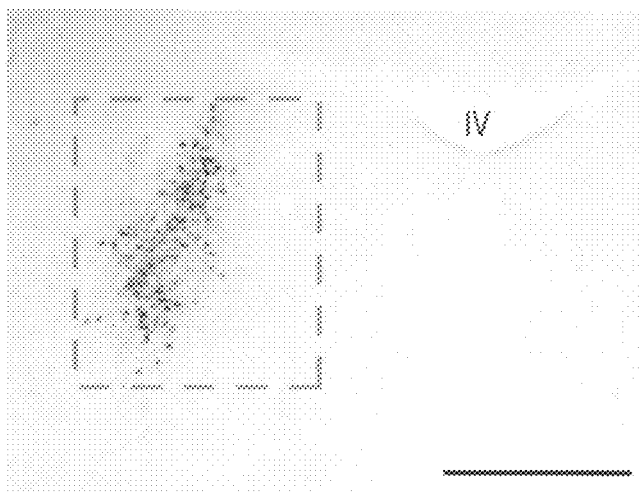 
FIG.5A
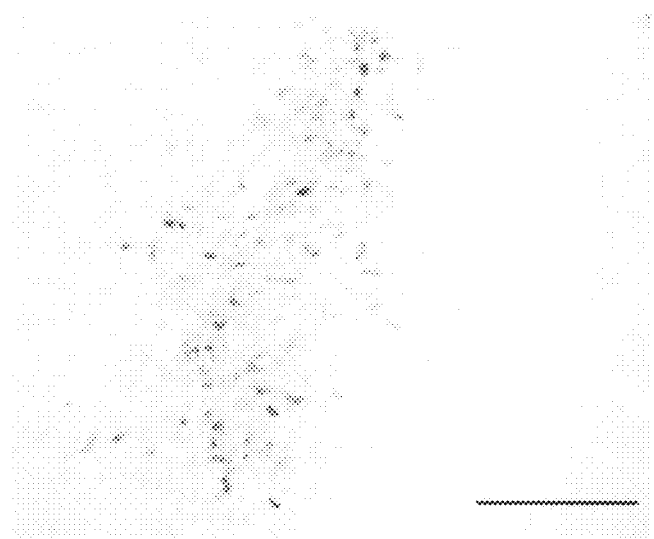 
FIG.5B
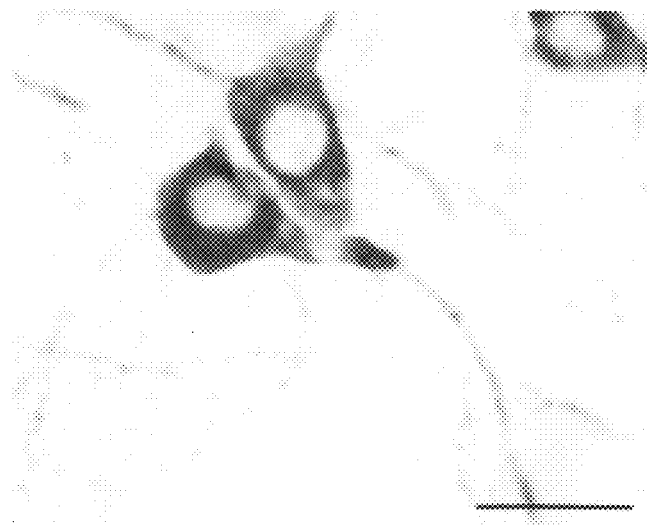
FIG.5C

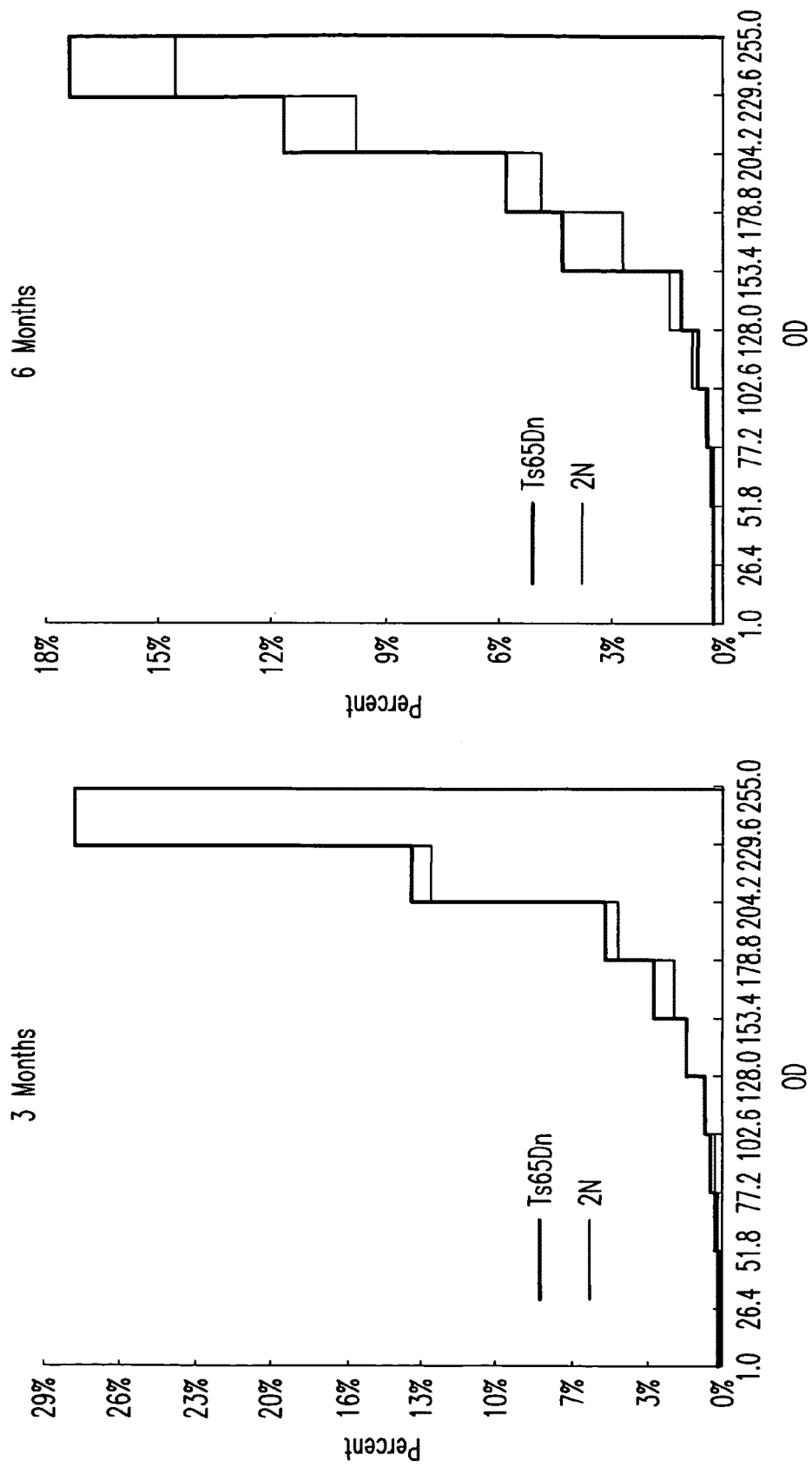

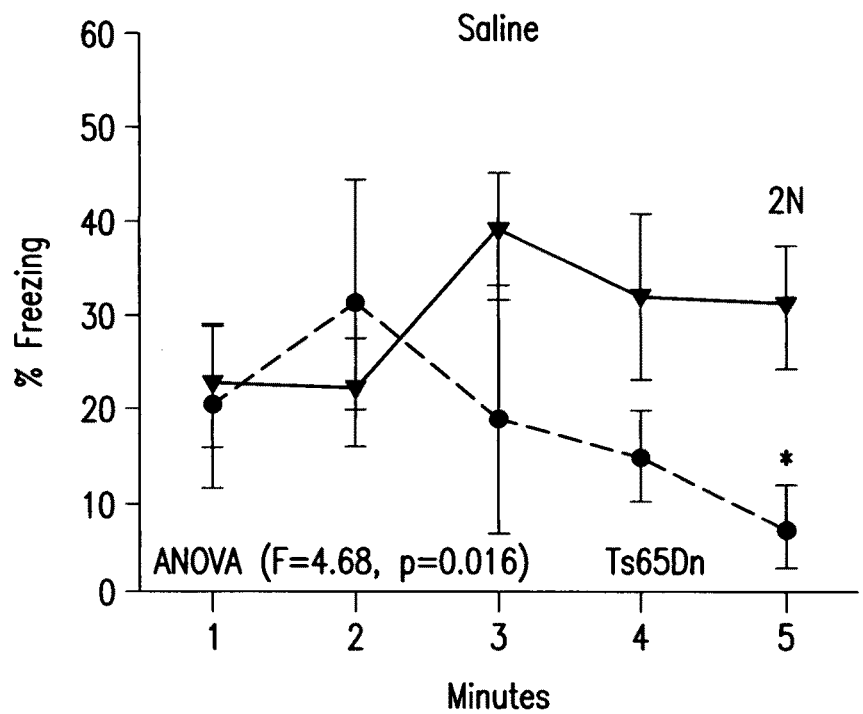
FIG.12A
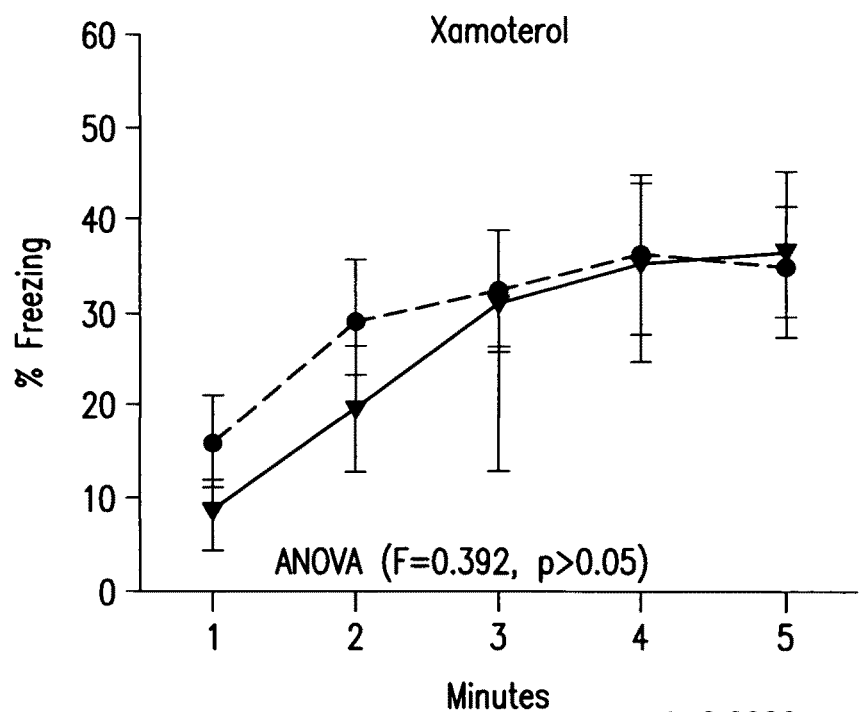
FIG.12B  *=0.0082

METHOD OF IMPROVING COGNITIVE FUNCTIONS IN INDIVIDUALS WITH DOWN SYNDROME AND/OR ALZHEIMER'S DISEASE

CROSS-REFERENCE TO RELATED APPLICATIONS

This application claims priority to provisional application, U.S. Ser. No. 61/213,173, filed on May 14, 2009.

FIELD OF THE INVENTION

The present invention provides a method of improving cognitive functions in individuals with Down syndrome and/or Alzheimer's Disease and/or Parkinson's Disease or other diseases or conditions that would result in degeneration of locus coerulus (LC).

DESCRIPTION OF THE BACKGROUND

Down syndrome (DS) is a complex genetic disorder caused by a third copy of chromosome 21 resulting in triplication of ~300 genes. It is the most common source of congenital anomalies with a prevalence of 1 per 733 live births in the US, resulting in the birth each year of 5,000 affected infants. Among several abnormalities occurring with DS, intellectual deficiencies that affect the quality of life for both children and adults is a primary concern. Understanding the neurobiological basis of failed cognition in DS is, thus, a high priority with the hope that deciphering pathogenesis will lead to effective therapies.

Failed learning and memory is essentially universal in people with DS. We have pursued a strategy that emphasizes the initial documentation of phenotypes followed by discovery of underlying gene dose effects and molecular and cellular mechanisms. The hippocampus (HC) is markedly affected in DS. This brain region is essential for registering events with respect to time and space. By modulating contextual discrimination, in which spatial information is integrated with other salient features of the environment, the HC mediates appropriate responses to dynamic changes in milieu. Among the many deficits present in children with DS, these individuals show severe defects in contextual tasks mediated by hippocampus. This phenotype is both robust and significant compromising the ability to carry out tasks of daily life. Interestingly, cued recall, in which memory is elicited by certain sensory cues is spared in DS; these tasks are modulated by amygdala and, unlike HC, this region shows no change in structure in young people with DS.

Individuals with DS may have some or all of the following physical characteristics: oblique eye fissures with epicanthic skin folds on the inner corner of the eyes, muscle hypotonia (poor muscle tone), a flat nasal bridge, a single palmar fold, a protruding tongue (due to small oral cavity, and an enlarged tongue near the tonsils), a short neck, white spots on the iris known as brushfield spots, excessive joint laxity including atlanto-axial instability, congenital heart defects, excessive space between large toe and second toe, a single flexion furrow of the fifth finger, and a higher number of ulnar loop dermatoglyphs. Most individuals with DS have mental retardation in the mild (IQ 50-70) to moderate (IQ 35-50) range, with individuals having mosaic DS typically 10-30 points higher. In addition, individuals with DS can have serious abnormalities affecting other body systems.

Since the majority of individuals with DS fall into the mild to moderate range of cognitive impairment, it has been estimated that even a small, perhaps, 10-20% improvement in cognitive functions could provide a significant number of these individuals with the ability to live independently rather than dependently.

Almost all individuals with DS will show Alzheimer's disease (AD) brain pathology after the age of 40. Furthermore, in a number of these cases dementia is exhibited.

While efforts have been made to improve cognitive ability in individuals having DS using vitamin E, studies have demonstrated that high doses of vitamin E may pose serious health risks. Furthermore, drugs with ability to increase the levels of brain acetylcholine (e.g. Aricept) and approved for the use in people with AD, have been used in people with DS and shown moderate improvement in cognition.

Parkinson's Disease (PD) is a degenerative disorder of the central nervous system that often impairs the motor skills, speech and other functions of afflicted individuals. While many forms of PD are idiopathic, i.e., no known cause, so-called secondary PD cases may arise from toxicity due to drugs, head trauma or other disorders. PD also causes neuropsychiatric disturbances, which include mainly cognition, mood and behavior problems.

It is known that symptoms of Parkinson's disease result from the greatly reduced activity of dopaminergic cells in the pars compacta region of the substantia nigra. This disruption of dopamine pathways is considered to be a likely explanation of much of the neuropsychiatric pathology associated with PD. Generally, in PD, neurons normally producing dopamine fail to function properly. The motor symptoms may include trembling of the hands, arms, legs and trunk; stiffness of the arms, legs and trunk; slowness of movement; and poor balance and coordination. Most commonly, PD commences at the age of about 60 years, but can begin at an earlier age. PD is more common in men than women. There is presently no known cure for PD.

Thus, a need exists for a method of treating individuals with DS and/or AD and/or PD to improve cognitive and/or motor ability in an effective manner without posing serious health risks.

SUMMARY OF THE INVENTION

Accordingly, it is an object of the present invention to provide a method for treating DS and/or AD and/or PD in mammals, particularly humans.

It is, moreover, an object of the present invention to provide a method for improving cognitive and/or motor functions in individuals exhibiting DS and/or AD and/or PD.

It is further an object of the present invention to provide a method for at least partially correcting deficient norepinephrine (NE) transmission in humans exhibiting DS and/or AD and/or PD.

It is also an object of the present invention to provide a method for improving cognitive functions in a mammal exhibiting a disease or condition that resulted from degeneration of the locus coerulus (LC).

It is, moreover, an object of the present invention to provide a method for improving motor functions in a mammal exhibiting symptoms of PD.

Accordingly, the above objects and others described are provided by a method for improving cognitive impairment in a mammal exhibiting DS and/or AD or symptoms thereof, which entails administering to the individual an amount of one or more compounds or salts thereof which at least partially restore cognitive ability of the mammal by increasing hippocampal NE levels.

The above objects and others described are also provided by a method for improving motor functions in a mammal exhibiting PD or symptoms thereof, which entails administering an amount of one or more compounds or salts thereof which at least partially restore motor function or at least partially reduce symptoms of PD in the mammal by stimulating production of dopamine in dopaminergic neural cells.

BRIEF DESCRIPTION OF THE DRAWINGS

FIG. 5. Immunocytochemical visualization of TH-positive neurons in LC region. Scale bar=500 µm (A), 200 µm (B) and 20 µm (C). IV; 4th ventricle.

FIG. 9. Frequency distribution of β1-adrenergic receptor immunoreactivity in the entire hippocampus in 3 and 6 months old Ts65Dn mice and their 2N controls. Unlike 3-months-old mice, there was a trend toward higher density in β1-adrenergic receptor immunoreactivity in Ts65Dn mice in 6 months old mice.

FIG. 12. Percent of freezing in the third (contextual) day in 2N and Ts65Dn mice treated with saline or β1-adrenceptor partial agonist xamoterol. Saline-treated T65Dn mice failed to recognize the context (ANOVA F=4.68, p=0.016). However, treating these mice with xamoterol one hour before the testing showed that Ts65Dn mice showed significant restoration of contextual discrimination and no longer any differences were found between 2N and Ts65Dn mice (ANOVA F=0.392, p=0.844).

DETAILED DESCRIPTION OF THE PREFERRED EMBODIMENT

Figure 1A:
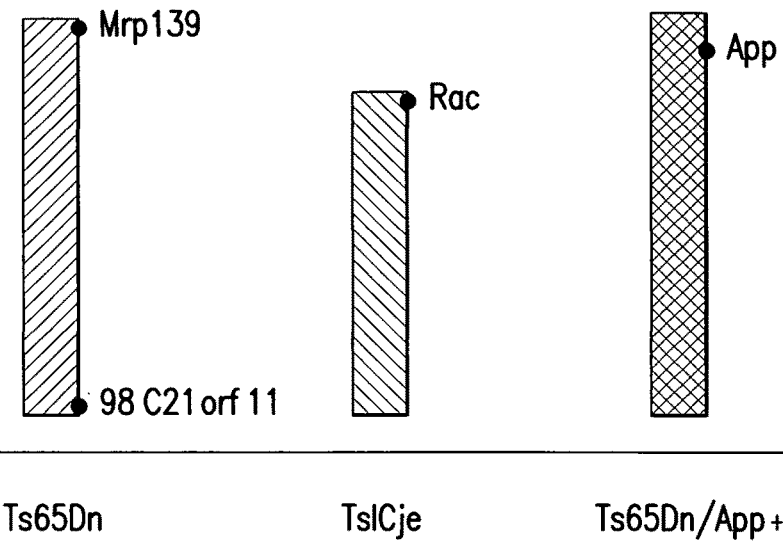
FIG. 1. Contextual learning and its restoration in mouse models of DS. A) Schematic representation of trisomic regions in mouse models of DS used for this study. B) No significant differences were found between 2N and Ts65Dn mice treated with carbidopa (CD) in cued learning tests. However, there was a significantly shorter freezing time in Ts65Dn mice in the contextual day as compared with 2N mice. C-D) Quantifying the percent of freezing during the first 5 minutes in contextual day, indicated that, unlike Ts65Dn mice, the 2N group improved drastically with each minute (One-way ANOVA p=0.0002). Treating 2N and Ts65Dn mice with L-DOPS led to a significant improvement in contextual memory in Ts65Dn mice. As the result, there was no significant difference between the two groups (One-way ANOVA p=0.5247). E) Ts65Dn mice used significantly lower amounts of their nestlets compared with 2N mice. Treating the mice with L-DOPS led to a significant improvement in the nesting behavior in Ts65Dn mice. The beneficial effects of L-DOPS vanished 2 weeks later.

Term Definitions as used herein:
HC=hippocampus
EC=entorhinal cortex
GABA=γ-aminobutyric acid
BFCNs=basal forebrain cholinergic neurons
NE=norepinephrine
LC=locus coerulus (or ceruleus)
AD=Alzheimer's disease
DS=Down syndrome
BBB=blood brain barrier
NRI=norepinephrine reuptake inhibitor(s)
PD=Parkinson's Disease
Prodrug=This means a derivative of a drug molecule that requires a transformation in the body to release the active drug. An amino group-containing active drug, such as the compounds described herein in accordance with the present invention, may be converted to a carbamate, amide, enamine, imine, N-phosphonyl, N-phosphoryl or N-sulfenyl prodrug which may be hydrolyzed in vivo to provide the amino group-containing active drug. Preparatory procedures and reactions for preparing such prodrugs are well-known to those of ordinary skill in the art. Also see, U.S. Pat. No. 7,227,028, which is incorporated herein in the entirety.

β1 adrenergic or adrenoreceptor agonist=This means a compound or salt thereof that binds to, or interacts with, β1 receptors with stimulation thereof to enhance receptor activity. An antagonist has the opposite effect.

Symptoms of DS=There are more than 50 symptoms of DS, including short physical stature, weak muscles, single crease along palms of hands (transverse palmar crease), facial features, such as small low set ears and irregularly-shaped mouth and tongue; and cognitive disability.

Symptoms of AD=Symptoms of AD, which also function as warning signs, include memory changes that disrupt daily life, challenges in planning or solving problems, difficulties in completing familiar tasks at home, confusion with time or place, difficulty in understanding visual images and/or spatial relationships, new problems with words in speaking or writing, misplacing objects and changes in mood/personality.

Symptoms of PD=Trembling of the hands, arms, legs or trunk, stiffness of the arms, legs or trunk, slowness of movement and poor balance and coordination.

Pharmaceutically-acceptable salts=This phrase means those salts of compounds of the present invention that are recognized as safe and effective for use in, and administration to, mammals, particularly humans and that posses and/or retain the biological/pharmaceutical activity of the compound as defined in the present specification. These salts are generally acid-addition salts and may include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate. It is further understood that where the term "salts" is used hereinbelow that term is used to mean "pharmaceutically-acceptable salts".

L-DOPS=the IUPAC name is (2R,3S)-2-amino-3-(3,4-dihydroxyphenyl)-3-hydroxypropanoic acid. There are four (4) stereoisomers of 3,4-dihydroxyphenylserine which have been separated by high-performance liquid chromatography (HPLC) with a chiral stationary phase based on a chiral crown ether. See Journal of Chromatography A, Volume 675, Issues 1-2, 22 Jul. 1994, pp. 244-247.

Threo-DOPS, which exists as a racemic DL-isomer and which is resolvable into two optical isomers, the L- and D-isomers. Threo-DOPS may be purchased from a chemical supply house or may be prepared according to the procedures described in U.S. Pat. No. 4,480,109, which is incorporated herein in the entirety. That incorporated U.S. patent also discloses various racemic syntheses as well as optically active syntheses and method of resolving optically active isomers.

Further, the term "improving cognitive functions of an individual" means an improvement based upon a baseline IQ measurement of the individual on a standardized intelligence test. This improvement also generally manifests itself in an ability of the individual to contextually learn as defined by standardized tests that measure such an ability. An improvement therein is also based on a baseline measurement. The improved cognitive ability is contemplated, for example, as sufficient to assist individuals exhibiting a disease or condition resulting in degeneration of the LC to be able to live independently rather dependently, which may require as little as a 10 to 20% improvement in cognitive ability.

The hippocampus (HC) is a major component of the human brain and belongs to the limbic system. The HIC plays a significant role in both long term and spacial navigation, and is closely associated with the cerebral codex and is located in the medial temporal lobe. Thus, the HC plays a critical role in a number of cognitive functions including, the registration of events with respect to time and space. By modulating contextual discrimination, in which spatial information is integrated with other salient features of the environment, the HC mediates appropriate responses to dynamic changes in milieu. Amnesic individuals with hippocampal damage fail in tests of contextual discrimination. Furthermore, hippocampal and entorhinal cortex (EC) damage has been shown to produce insensitivity to contextual changes in rodents, as has transient inactivation of HC using GABAA agonists. Contextual discrimination is made possible by accessing information from a number of afferent systems, both sensory and modulatory; sensory information is transmitted from EC while modulatory inputs originate in several populations including basal forebrain cholinergic neurons (BFCNs), norepinephrine-ergic (NE-ergic) neurons of locus coeruleus (LC), serotoninergic neurons of raphe nuclei, and calretinin-positive neurons of supramamillary area. Modulatory inputs extensively innervate the HC (see FIG. 1A). With respect to contextual discrimination, LC, which is the sole source of NE-ergic inputs, appears to play a defining role through the release of NE to act on β adrenoceptors. Indeed, studies in which the activity of LC afferents or B1 receptors were selectively targeted, showed NE-ergic neurotransmission is essential for this aspect of hippocampal function.

While it was unknown prior to the present invention whether or not LC plays a role in contextual learning in humans, the present invention is predicated, in part, upon this discovery. Essential to demonstrating this link were studies that dissect hippocampally-driven contextual learning from cued learning, in which amygdala plays a central role. Examining disorders in which LC degenerates is one strategy for exploring LC function in humans. This population is markedly affected in AD, DS, Parkinson's disease, Huntington's disease, dementia pugilistica, and Wernicke-Korsakov syndrome. Interestingly, in AD, LC neurons undergo more extensive degeneration than BFCNs and the extensive neurofibrillary degeneration of LC correlates well with the severity of cognitive decline. Further, NE levels have been found to be significantly reduced in temporal cortex. In DS, individuals show significant hippocampal dysfunction, including deficits in contextual discrimination. While cued learning remains in tact, contextual learning is markedly impaired in both infants and adolescents with DS. Such deficits appear to significantly impair learning.

To explore what role, if any, LC degeneration plays in contextual discrimination in DS, we examined mouse models of this disorder. Herein, we describe our discovery that with progressive degeneration and dysfunction of LC neurons the presence of marked deficits in tests that measure contextual discrimination was demonstrated. Significantly, because the postsynaptic hippocampal targets of degenerating neurons demonstrated continued responsiveness to NE, we increased hippocampal NE levels through treatment of mice with an NE prodrug or by delivering a β1 agonist. The result was full rescue of contextual deficits. These findings evidence that LC dysfunction contributes significantly to cognitive dysfunction in DS and points to the efficacy of NE-based treatments for DS and other disorders in which there is degeneration and dysfunction of LC, such as AD.

Thus, in one aspect the present invention provides a method for at least partially restoring contextual learning ability in individuals suffering from DS and/or AD.

In another aspect, the present invention provides a method for at least partially restoring NE-ergic transmission in individuals thereby deficient.

The present invention also provides a method for stimulating postsynaptic targets of degenerating neurons in an individual having a disease or impaired condition of presynaptic inputs thereof to improve cognitive ability.

In effecting any of the above methods or combinations thereof; one or more compounds or pharmaceutically acceptable salts thereof which at least partially restore contextual learning and/or at least partially restore deficient NE-ergic transmission and/or stimulate postsynaptic targets of degenerating neurons are administered to an individual exhibiting any or all of these conditions.

More particularly, it has been discovered that compounds which are immediately upstream of NE in the in vivo synthesis of NE, are advantageously used in accordance with the present invention.

The in vivo catecholamine synthesis pathway involves the following steps: 1) L-Tyrosine is converted by means of tyrosine hydroxylase to L-Dihydroxyphenylalanine (L-DOPA); 2) L-DOPA is converted by means of DOPA decarboxylase to dopamine; 3) Dopamine is converted by means of dopamine beta-hydroxylase to Norepinephrine (NE); and 4) NE is converted by means of Phenylethanolamine N-methyltransferase to epinephrine.

In accordance with the present invention, the use of more upstream catecholamine compounds is avoided. For example, both dopamine and L-DOPA are upstream of NE and Epinephrine. L-DOPA is converted into Dopamine which causes significant modulation of motor functions. Generally, the more upstream the compound is from NE, the more side effects are generated due to activation of other systems, i.e., dopaminergic, than NE.

L-Tyrosine is upstream to all catecholamine compounds, including dopamine, NE and epinephrine. Hence, use of L-Tyrosine is avoided in accordance with the present invention as it causes an increase in L-DOPA, dopamine as well as NE with attendant side effects.

Similarly, known drugs that stimulate the indiscriminate production of catecholamines are avoided in accordance with the present invention for the same reason. For example, Tolcapone is a COMT inhibitor involved in the metabolism of dopamine, NE and epinephrine and is not used in accordance with the present invention due to consequent production of catecholmires upstream from NE.

The one or more compounds may be either an NE-prodrug, i.e., a prodrug of norepinephrine or a β1 agonist. The term "prodrug" may also be used to define various derivative compounds of any amino group-containing compounds as described herein which may be transformed in vivo to release the amino group-containing active compound in the mammalian body.

Examples of NE-prodrug may include, for example L-threo-3,4-dihydroxylphenylserine (L-DOPS) or any compound that is metabolized by LC terminals to release NE. Such compounds also readily cross the blood brain barrier (BBB).

Examples of β1 adrenoreceptor agonists may include, xamoterol or other compounds which bind to the β1 adrenergic receptor, i.e., β1 adrenoreceptor agonists that easily cross the BBB.

Generally, the NE prodrugs or β1 adrenoreceptor agonists ate administered as compounds, pharmaceutically acceptable salts thereof, such as hydrochlorides, sulfates, phosphates, citrates, fumarates or phosphates and as more generally defined above. However, these compounds or salts thereof may be administered as pharmaceutical compositions containing one or more of the NE prodrug or β1 adrenoreceptor agonists or salts thereof in combination with a pharmaceutical acceptable carrier, such as dextrose 5% saline solution. Preferably, the compounds or compositions containing them are administered by injection.

Further, compositions containing L-DOPS or another NE prodrug used therefor or in addition thereto may be formulated in accordance with U.S. Pat. No. 4,330,558, which is incorporated herein in the entirety by reference.

NE has the IUPAC name 4-(2-amino-1-hydroxyethyl)benzene-1,2-diol. The natural isomer is L-(−)-(R)-norepinephrine and has the following formula:

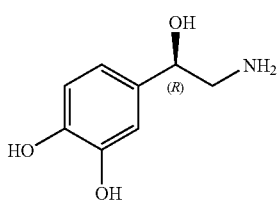 [SMILES: NC[C@H](O)c1ccc(O)c(O)c1]

Other examples of NE prodrugs may include lower alkyl esters of any or all of the three hydroxyl (—OH) groups in the above formula where the lower alkyl ester group —R would replace any or all of —H of the hydroxyl groups. Examples of —R are, Methyl ester, ethyl ester or n-propyl esters.

Similarly, other examples of NE prodrugs may include lower alkyl esters of the amine (—NH2) group in the above formula, where one or both —H atoms may be established by —R, wherein R may be methyl ester, ethyl ester or n-propyl ester.

With any of the above norepinephrine esters and/or amides, NE is released in the body upon hydrolysis of the esters and/or amides.

Compositions containing xamoterol or another β1 adrenoreceptor agonist used therefor or in addition thereto may be formulated in accordance with U.S. Pat. No. 4,933,340, which is incorporated herein in the entirety by reference.

Of course, compositions may be formulated which contain both NE prodrug and β1 adrenoreceptor (or adrenergic receptor) agonists. Examples of such agonists are dopamine and dobutamine and the pharmaceutically-acceptable salts thereof, such as phosphate, sulfate, chloride, acetate or citrate, for example, and as more generally defined above. All of these agonist compounds are known and may be purchased from a pharmaceutical supply house or synthesized using well-known procedures. The salts, of course, may be produced using well known acid addition reactions.

To explore the pathogenesis of cognitive disabilities in DS, we carried out studies in the Ts65Dn mouse of model of DS. This mouse is trisomic for a fragment of MMU16 extending from Mrpl39 to 98C21orf11 (FIG. 1A); it contains at least 104 mouse genes homologous to those present in three copies in DS. Ts65Dn mice recapitulate a variety of DS structural and functional changes. To investigate whether or not these mice show changes in contextual learning, we compared the performance of euploid (i.e. 2N) mice with Ts65Dn mice in fear conditioning test (FIGS. 1B-C). The contextual fear conditioning test, which registers fear-based responses as episodes of behavioral freezing, differentiates between contextual and cue-based learning. Following training on day 1, Ts65Dn and 2N mice underwent a test of cued learning on day 2 and contextual learning on day 3. We found no abnormalities in cued learning in Ts65Dn mice (p=0.1825, FIG. 1B). In contrast, there was a marked failure in Ts65Dn mice in contextual learning (p=0.0324, FIG. 1B). Indeed, in this test, while 2N mice showed twice as much freezing as compared to the training session, Ts65Dn mice showed no increase.

Nesting behavior is another test that measures hippocampally-based cognition. Prior studies have shown that nesting behavior can be used to define the integrity of hippocampal function. It has been shown to correlate with failed contextual discrimination and spatial learning in rodents. In tests of nesting, mice placed in a novel cage were provided with nesting material in the form of 'nestlets' of known weight (see methods; Fig. S1). Unlike 2N mice, Ts65Dn mice used relatively little of their nestlets (p=0.0012, FIG. 1E) and their nests were poorly formed. These findings are evidence that hippocampal function, and context discrimination in particular, are markedly affected in Ts65Dn mice.

Contextual learning requires the participation of locus coeruleus (LC). LC is the sole source of the NE-ergic inputs that engage 13 adrenoceptors in HC. Indeed, studies in which the activity of LC afferents or β1 receptors were selectively targeted, showed NE-ergic neurotransmission is essential for this aspect of hippocampal function. Whether or not LC plays a role in contextual discrimination in humans is yet to be defined but this population is markedly affected in a number of disorders, including elderly patients with DS and in those with AD, Parkinson's disease, Huntington's disease, dementia pugilistica, and Wernicke-Korsakov syndrome. Interestingly, in AD, LC neurons undergo extensive degeneration that correlates well with the severity of cognitive decline in these patients and NE levels have been found to be significantly reduced in temporal cortex.

Figure 2A:
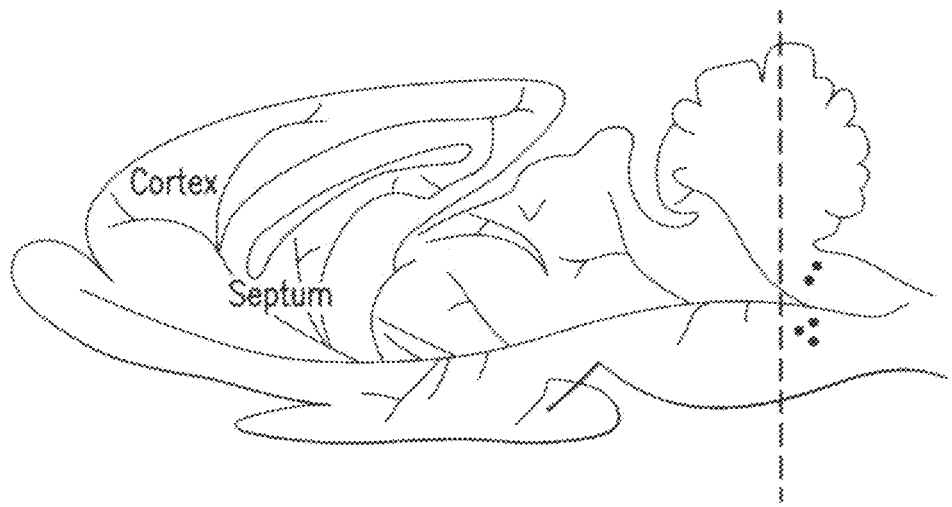
FIG. 2. Morphological and biochemical basis of failed NE system. A) The anatomical localization of NE-ergic neurons in the rodent brain. B) Micrographs depicting immunocytochemical visualization of LC in 2N and Ts65Dn mice at the age of 6 months using TH antibody. Scale bar=1 mm). No significant reduction was found in TH-positive neurons number (C) and cell profile area (D) in LC at 3 months of age. However, at the ages of 6 and 18 months, there was significant reduction in Ts65Dn mice compared with age-matched 2N controls. E) A significant decrease in the amount of VMAT2 staining was found in the DG of 6-month-old Ts65Dn mice. F) There was 16% reduction in the average concentrations of NE in 4.5 month-old Ts65Dn mice compared with 2N. However, there was a significant reduction in the concentrations of NE in the HC of 18-month-old Ts65Dn mice compared with 2N mice. It appears that there is also a loss of NE in the HC of both 2N (31%) and Ts65Dn (53%) mice. However, Ts65Dn mice lost more significant amounts of NE during aging (young Ts65Dn vs old Ts65Dn p=0.019). G) There was a significant increase in the total number of β1 positive neurons in the DG in Ts65Dn mice at age 6 months.
Figure 2B:
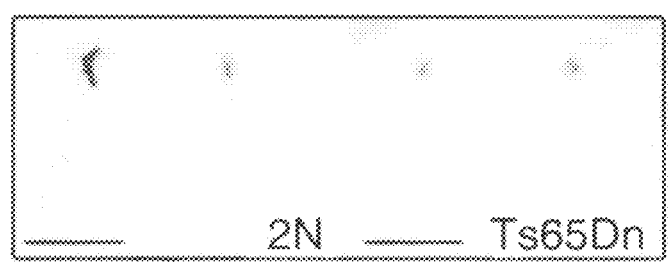
Figure 2C:
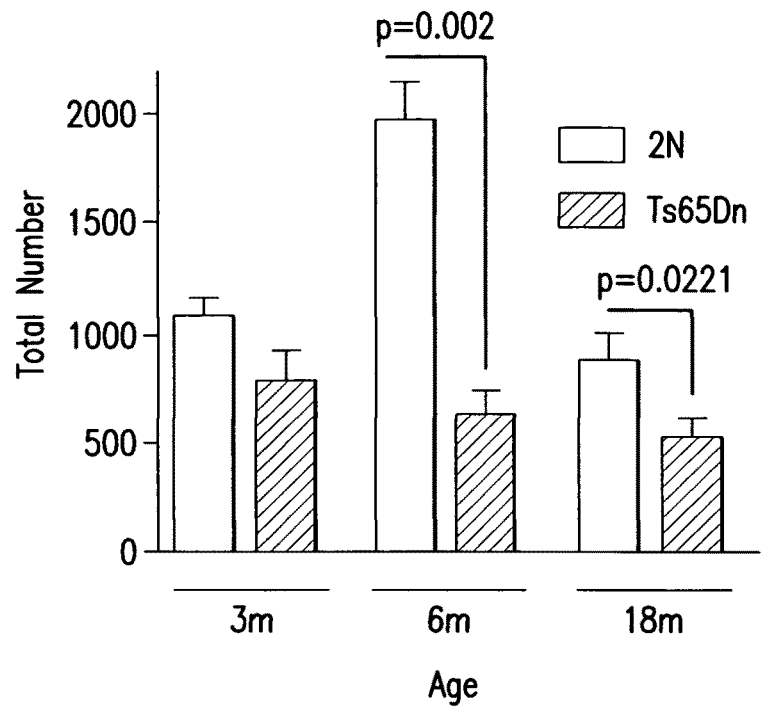
Figure 2D:
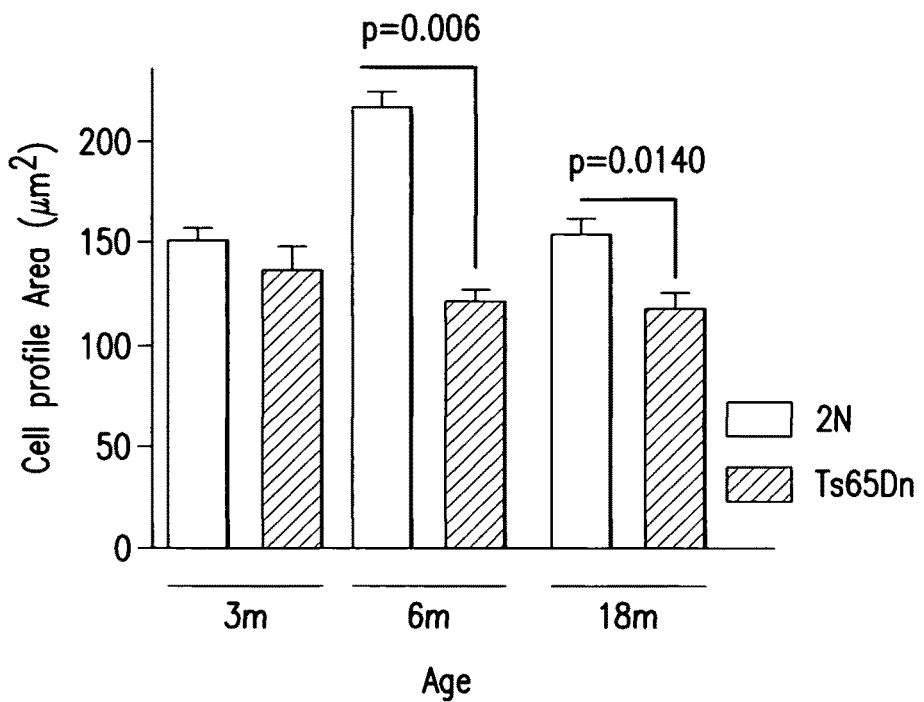

Given similar deficits in contextual learning in DS and the mouse model, we asked if LC degeneration was also present. Using an antibody against tyrosine hyrdoxylase (TH), NE-ergic neurons were examined throughout the rostro-caudal axis of the LC. Unbiased stereology (see methods) was used to estimate the total number and cell profile area of TH-immunoreactive (TH-IR) neurons in LC (FIGS. 2A-D & S2). We first examined mice at 6 months of age because this age was used for behavioral testing. TH-IR cell number was significantly lower in Ts65Dn mice at this age. A similar pattern was observed in the size of TH-IR cell profile areas (FIGS. 2D, S3A). Studying mice at ages before and after 6 months showed that the degeneration of LC neurons persisted at 18 months, while in 3 month-old mice, there was no significant difference in either parameter. The temporal pattern of changes was reminiscent of those documented for BFCNs in Ts65Dn mice, in that the differences were due both to a decrease in the umber of neurons and failure to show an increase in number with aging. The latter almost certainly reflects a failure to increase TH content in NE-expressing neurons in Ts65Dn mice.

LC innervates most brain regions; its projections are organized topographically. The anterior pole of LC innervates the hypothalamus while the posterior supplies the HC. The neurons between the poles innervate HC, cerebellum, cortex, and spinal cord (Fig. S3B). We examined the possibility that changes in LC cells would differentiate the different regions of this area. The severity of degeneration in Ts65Dn mice was greatest in the caudal LC (Fig. S3C), a sub-region with extensive projections to the HC.

Figure 2E:
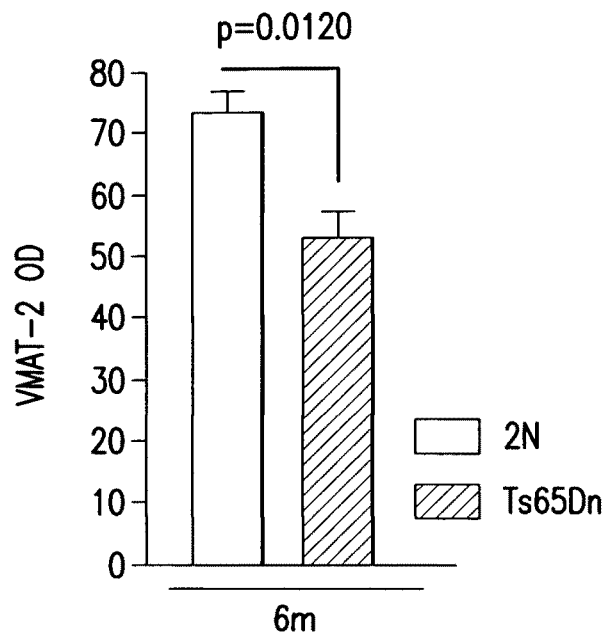

To ask whether changes in LC neuron cell bodies are linked to changes in HC innervation, we examined monoaminergic (MA)-terminals in HC by examining and quantifying staining for vesicular monoamine transporter (VMAT2). A majority of MA-ergic projections to the HC particularly in the DG, are NE-ergic. Comparing Ts65Dn and 2N mice at age 3 months, the DG of Ts65Dn mice showed a significant increase in VMAT2 staining; in particular there was a marked increase in the number of bright puncta (FIG. 2E). In contrast, by 6 months, the optical density of VMAT2 staining showed an overall decrease of –20% in comparison to 2N mice (FIGS. 2E & S4). These observations are evidence for changes in LC terminals that precede those detected in neuronal somas.

Figure 2F:
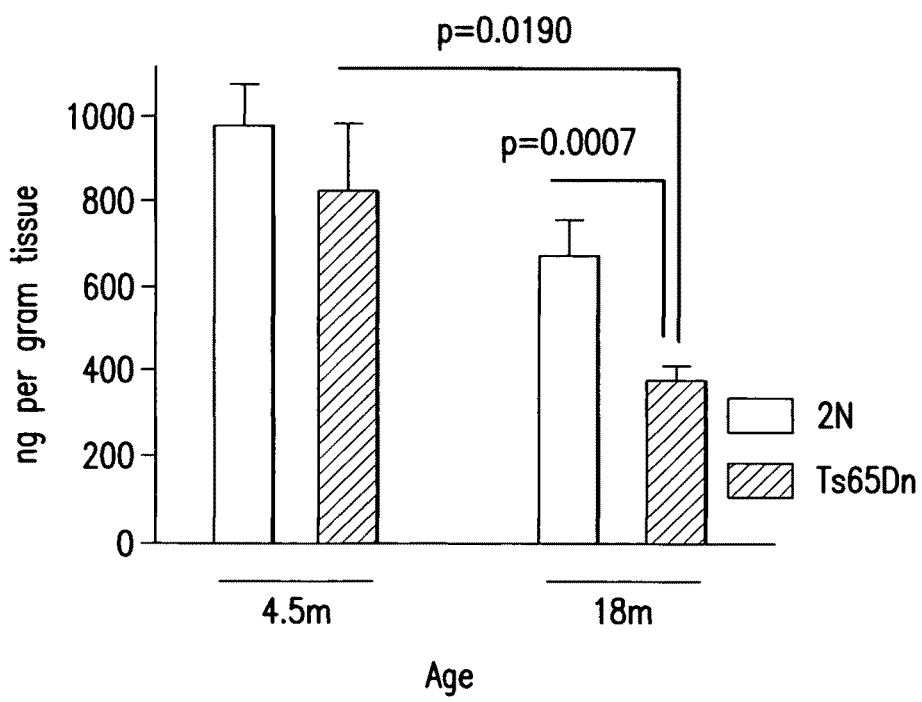

To determine whether or not the morphological change in axon terminals in HC was correlated with changes in NE, we examined the levels of this neurotransmitter. There was a significant age-related reduction in NE levels. Comparing the HC in Ts65Dn and 2N mice at 4.5 months of age, there was a 16% reduction in Ts65Dn that was not statistically significant. At 18 months, however, the decrease in Ts65Dn was significant (p=0.0007), averaging 31%. Examining absolute values for NE, there was a decrease with age in both 2N and Ts65Dn mice, but only the change in the Ts65Dn HC was significant (p=0.019; FIG. 2F). These findings gave additional evidence for dysfunction in the terminals of the LC neurons in Ts65Dn mice.

Next, we examined the postsynaptic targets of LC axons in HC. NE-ergic neurotransmission is affected in part through β1-adrenoceptors. The β1 receptor is present on the postsynaptic targets of LC axons in HC and has been shown to play an important role in cognition, including contextual discrimination. Hippocampal hilar neurons expressing β1 adrenoceptor gene; immunostaining for these receptors is readily detected on their cell bodies. In Ts65Dn mice at 3 months of age there was a marked increase in the size of β1-Ir cells (Fig. S5 6). The increase in size was also seen at age 6 months. At 6 months, we also documented a more than 90% increase in the number of β1-Ir neurons in the Ts65Dn HC (p=0.0173; FIG. 2G). At the same time, examining β1-Ir in the entire HC, we noted an overall increase that was significant (p<0.001). These findings are evidence for changes in the postsynaptic targets of LC neurons. Given the data in Ts65Dn mice for degenerative changes in LC terminals and reduced NE levels, the suggestion is raised of a compensatory increase in postsynaptic receptors in response to decreasing NE-ergic transmission.

Figure 3A:
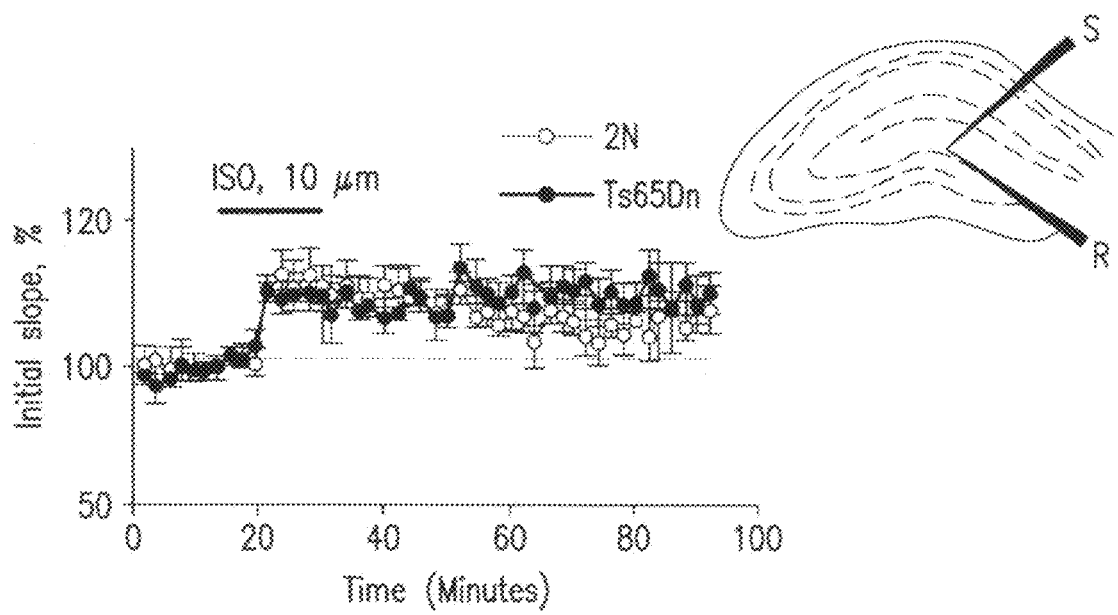
FIG. 3. Mechanisms underlying LC degeneration. A) Representative responses recorded from the granule cell layer following stimulation of the middle molecular layer before and after application of a β agonist; isoproterenol (ISO). The use of ISO generated stronger effects on slope of fEPSPs in Ts65Dn than 2N mice at the age of 6 months. B & C) Comparing contextual learning in Ts65Dn mice treated with saline or xamoterol showed a significant improvement in Ts65Dn mice (p=0.032). D) The LC neuron degeneration was significant only in Ts65Dn mice. This suggests that that the triplication of the region between Mrp/39, and Rac must be responsible for degeneration of LC neurons. E) There was a reduced size of TH-positive neurons in LC of Ts65Dn with three copies of App. Deleting an extra copy of App in Ts65Dn led to a shift to higher digits in the size of LC neurons. F) There was a significant decrease in the number of TH-positive neurons in LC of 18-month-old tg-APPSwe mice compared with WT mice.

The continued presence of NE receptors on postsynaptic targets raised the possibility that postsynaptic mechanisms activated by NE remained functional even with presence of LC dysfunction and degeneration. To test whether or not NE signaling would be registered in the DG of Ts65Dn mice, we studied the effect of isoproterenol (ISO), an agonist at both β1 and β2 receptors. For these studies, we applied stimulating current to the middle molecular layer of the DG in acute hippocampal slices, in the absence and presence of ISO, while recording in the DG granule cell layer. In slices taken at age 3 months, there were increase in both the slope and amplitude of excitatory postsynaptic potentials (EPSPs) in both 2N and Ts65Dn mice. The same was true at age 6 months. Remarkably, at age 6 months the responses in Ts65Dn slices were consistently more robust (FIGS. 3A and S7-8). Thus, responsiveness to NE was retained in spite of degenerative changes in LC neurons and their terminals in the HC.

Continued in vitro responsiveness of the targets of NE-ergic innervation suggested that the same might be true in vivo. To test the idea, we asked if restoring NE levels would rescue contextual fear conditioning in 6 month old mice. An NE prodrug was used that readily crosses the blood brain barrier (BBB). L-threo-3,4-dihydroxyphenylserine (L-DOPS) or droxidopa is a synthetic amino acid. L-DOPS is metabolized by L-aromatic amino acid decarboxylase within NE-ergic neurons to yield NE. To evoke NE increases in only the CNS, L-DOPS (1 mg/g) was administered together with carbidopa (CD, 0.125 mg/g), a peripheral DOPA decarboxylase inhibitor that does not cross the BBB. CD administration alone served as the control. L-DOPS levels were measured six hours after administration in both 2N and Ts65Dn mice. The drug was present in all tissues, including brain, with no difference between genotypes (p=0.4894). The NE levels in the HC of Ts65Dn mice reached to 96% of those in 2N mice. Because brain NE levels have been shown to reach their maximum levels within 5 hours of subcutaneous administration (14, 26), mice were tested at this time point. Treatment of 6-month-old Ts65Dn with 20 mg/ml L-DOPS led to a significant improvement in contextual memory (FIG. 1B-D). In the contextual test, L-DOPS restored fully the difference in freezing between 2N and Ts65Dn mice (FIG. 1C-D, One-way ANOVA p=0.5247). In the control group, in contrast a significant difference remained (One-way ANOVA p=0.0002). When performance was measured on a minute-by-minute basis, LDOPS treatment was associated with increased freezing following the first minute, a pattern shared with 2N mice treated as controls or with L-DOPS. A similar beneficial effect of L-DOPS was found in nesting behavior. Treating young adult Ts65Dn mice and their controls with L-DOPS significantly (p=0.0245) improved nesting in Ts65Dn mice (FIG. 1E). With cessation of treatment, Ts65Dn mice again showed poor nesting behavior (p=0.0121, FIG. 1E) These findings are evidence that contextual discrimination can be rescued in a mouse model of DS by increasing tissue levels of NE. They provide compelling support for the view that LC dysfunction markedly contributes to failure in contextual learning in this model.

Figure 3B:
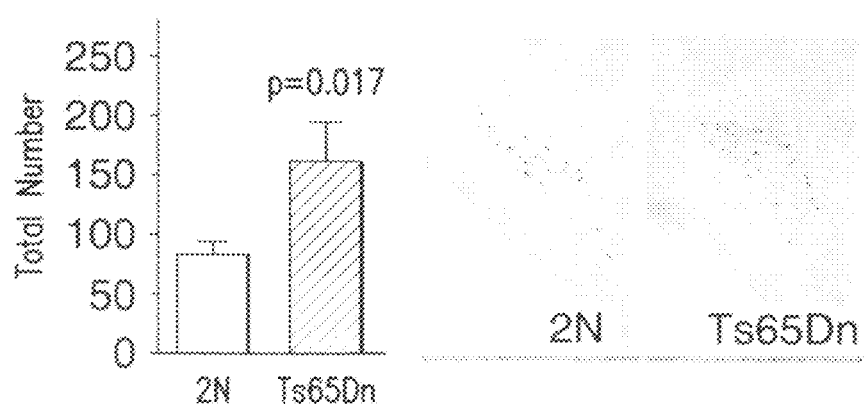
Figure 3C:
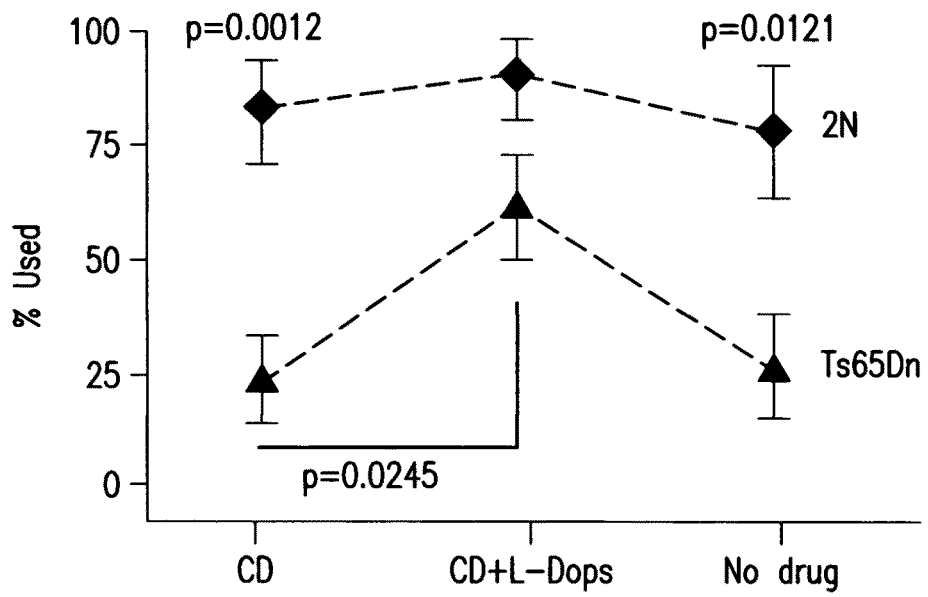

Increased B1-adrenoceptor expression raised the possibility that these receptors were involved in transducing the beneficial effects of L-DOPS in Ts65Dn mice. To test this idea, we treated Ts65Dn mice with xamoterol, a β1-adrenoceptor partial agonist. Comparing Ts65Dn mice and 2N controls, treatment with xamoterol during training restored failed contextual learning (FIGS. 3B-C & S9). These findings are evidence that p1-adrenoceptors play a vital role in mediating the effects of increasing NE-ergic transmission in the Ts65Dn hippocampus. Moreover, in extending the behavioral analysis, they show that pharmacologically targeting functionally intact postsynaptic neurons can restore contextual learning.

Figure 1B:
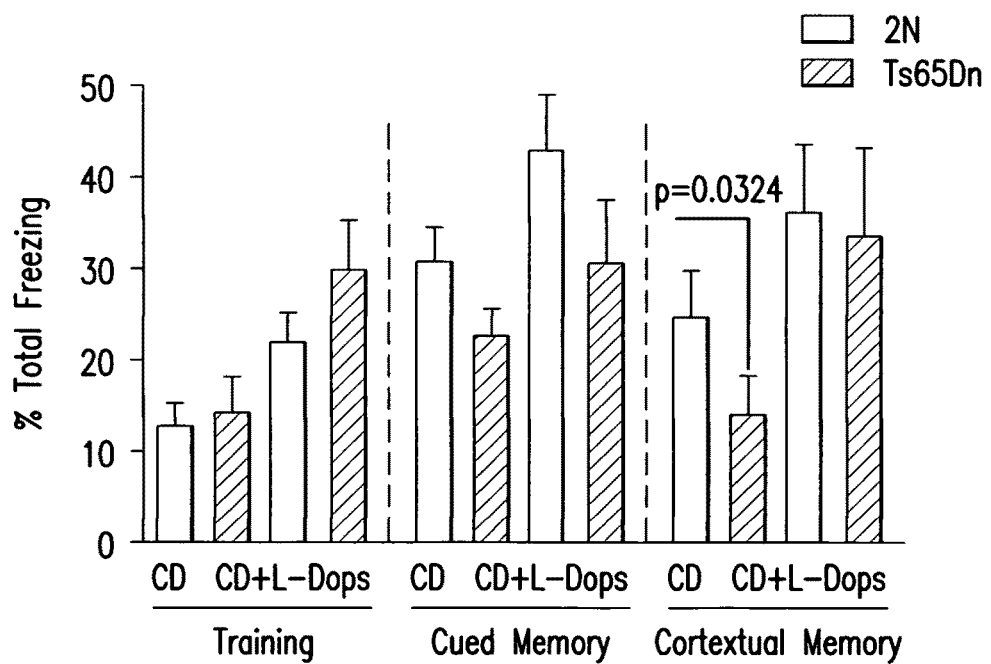
Figure 1C:
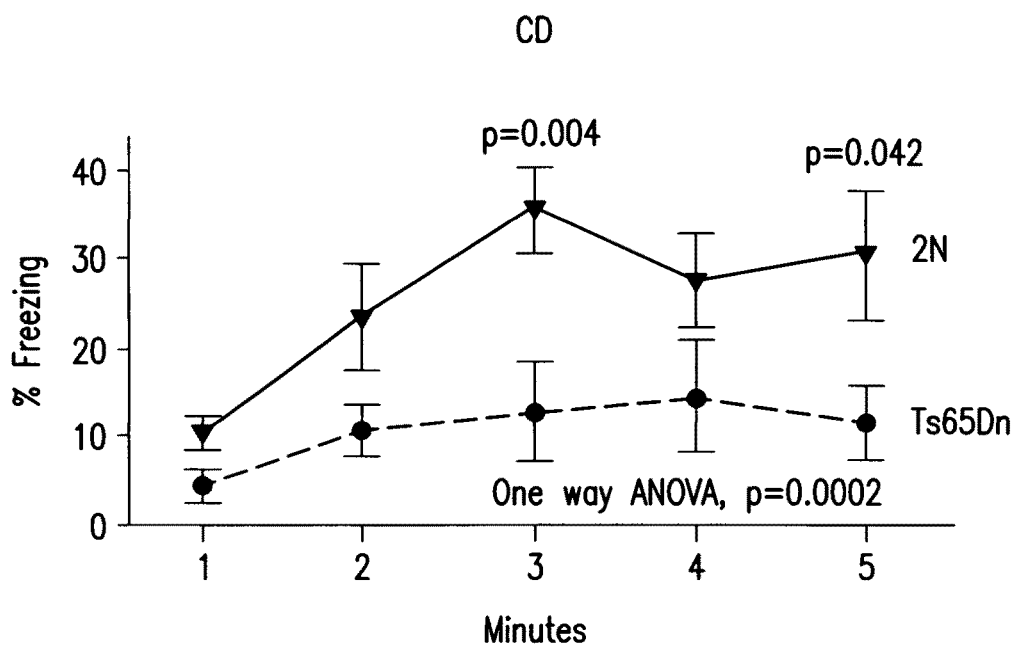
Figure 1D:
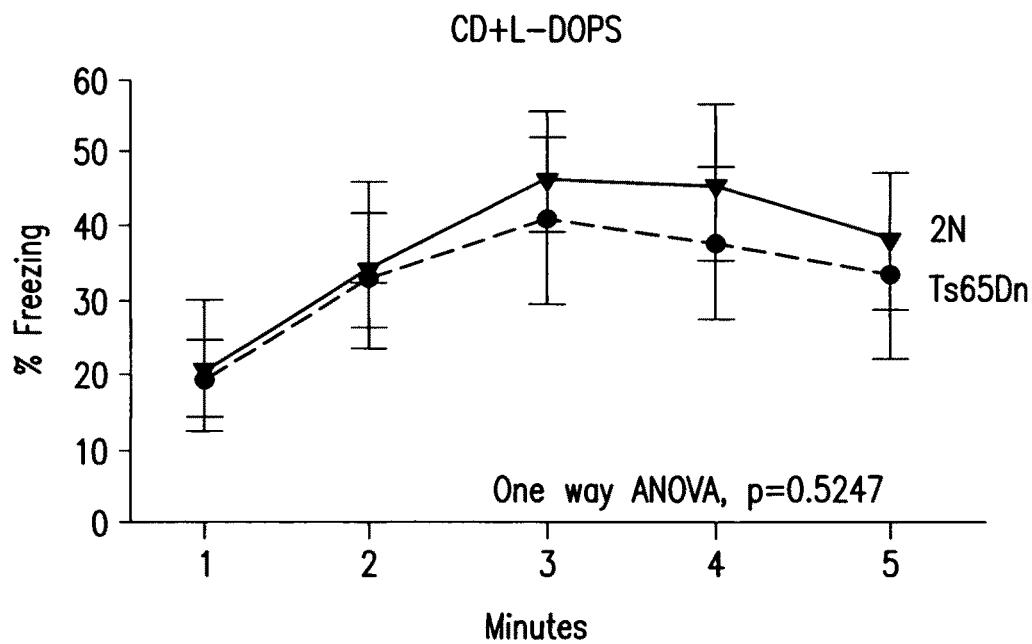
Figure 1E:
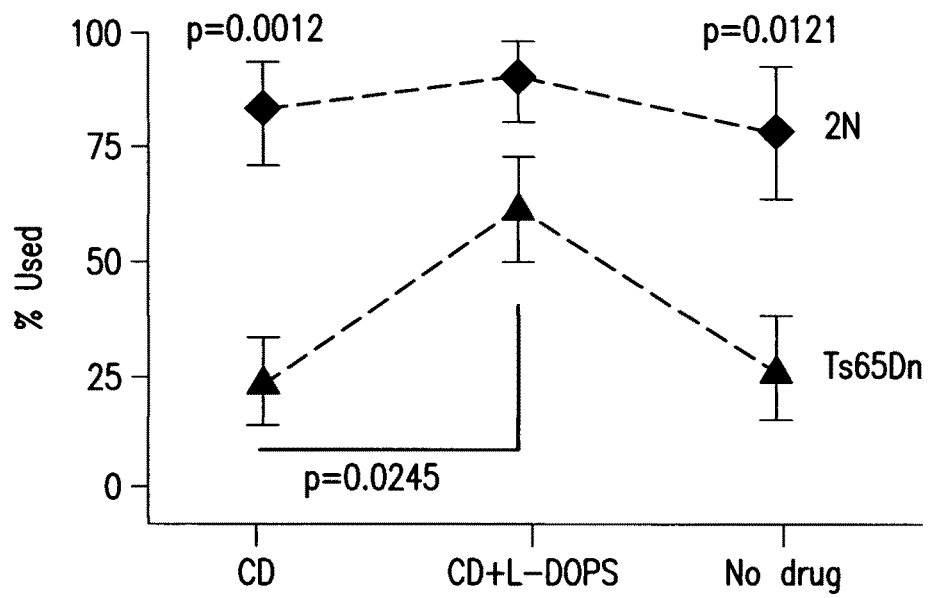
Figure 3D:
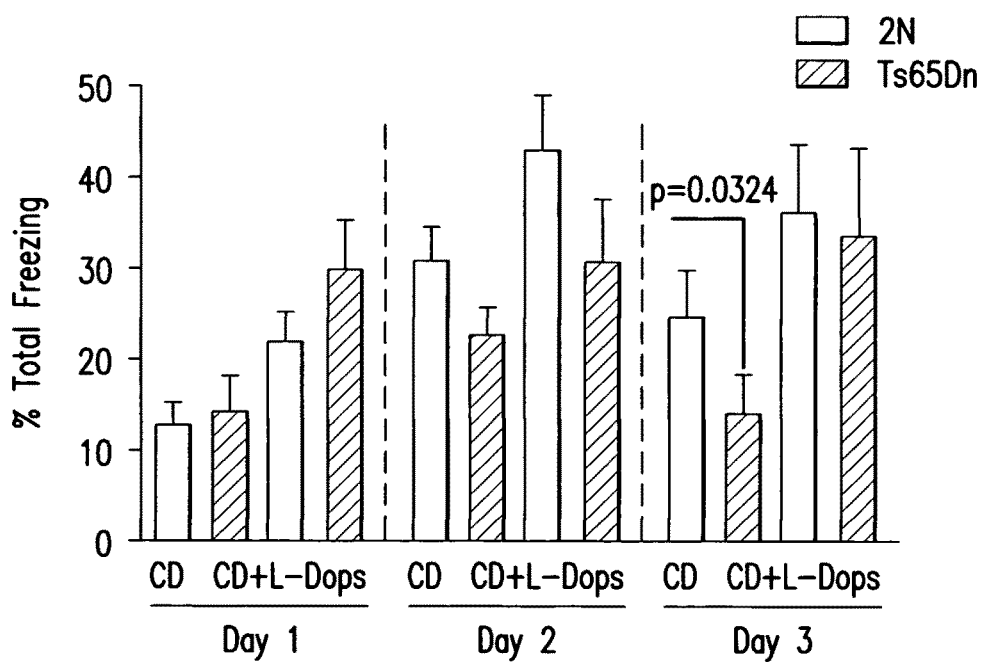
Figure 3E:
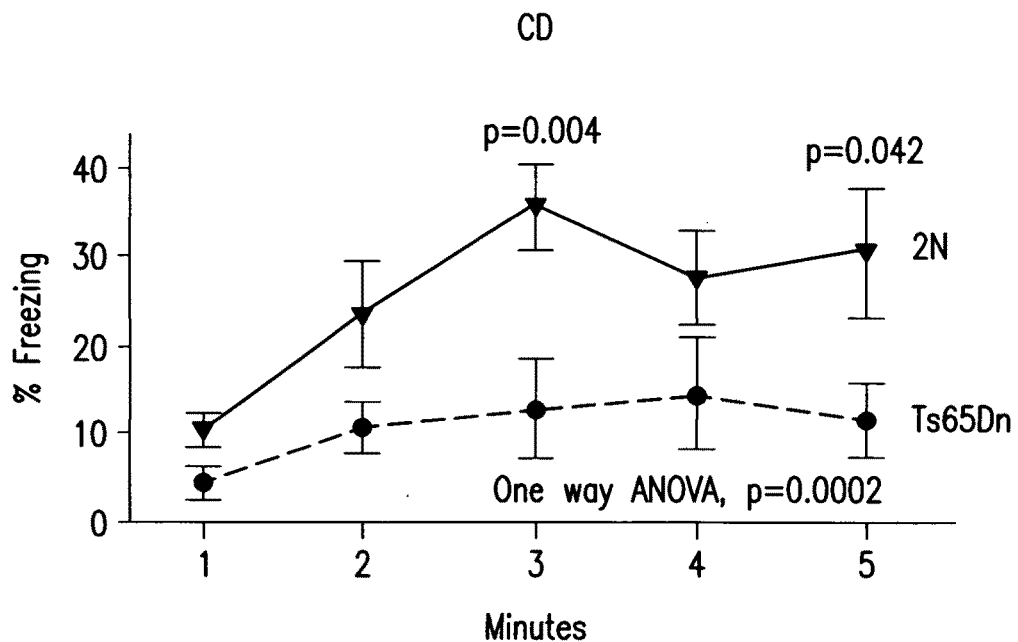
Figure 3F:
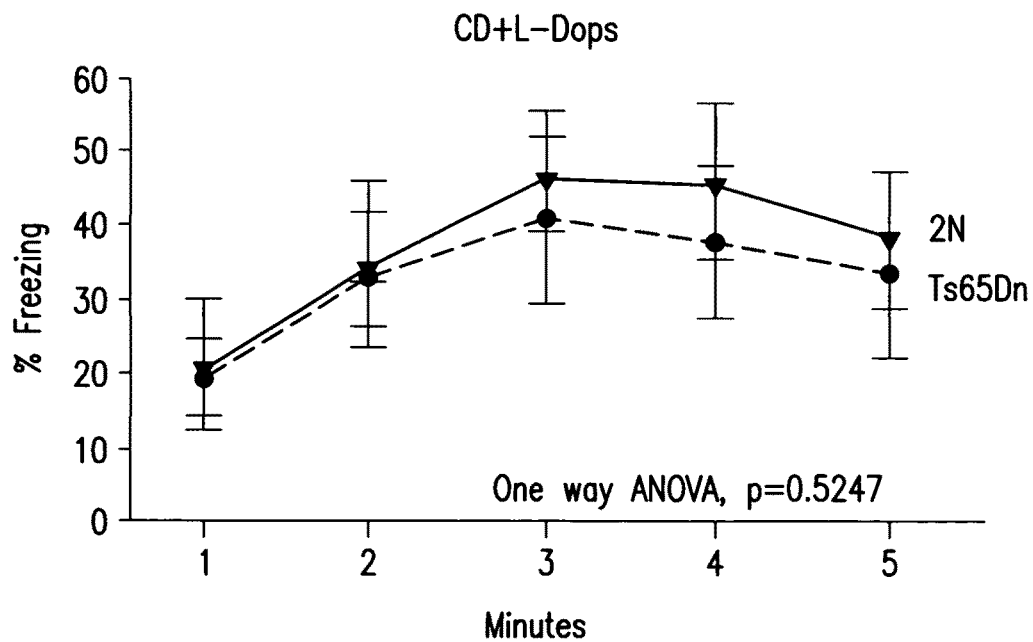

To decipher the underlying genetic basis for LC degeneration in Ts65Dn mice we compared mouse models of DS harboring different triplicated fragments of mouse chromosome 16 (MMU16, FIG. 1A). This approach has been use to identify a role for APP in the pathogenesis of BFCN degeneration in Ts65Dn mice. Even in old age, Ts1Cje mice showed no significant changes in size or number of LC neurons (FIG. 3D). The lack of apparent LC degeneration in Ts1Cje mice suggested the responsible gene(s) is located on MMU16 fragment between Gabpa and SodI (FIG. 1A); this region contains about 32 genes, including App. To test whether increased dose for App contributes to LC degeneration, we examined these neurons in Ts65Dn mice bearing either two or three copies of App. Deleting the third copy of App in Ts65Dn mice eliminated the decrease in the size of LC neurons, suggesting that App overexpression is necessary for LC degeneration (FIG. 3E). To ask whether or not App overexpression is sufficient to cause LC degeneration, we examined mice that overexpress a mutant APPSwe transgene. There was a significant decrease in LC neurons in these mice (p=0.0317, FIG. 3F). This latter finding is consistent with a recent report showing degeneration of LC neurons in APP/PS1tg mice. Taken together, the findings are evidence that APP gene dose plays a conspicuous role in the degeneration of LC neurons.

The present invention will be further illustrated by the following example which I provided solely for purposes of illustration and is not intended to be limitative.

In the following examples, (−) or L-threo-3-(3,4-dihydroxyphenylserine) was used as the isomer of L-DOPS.

Example 1

The Ts65Dn mouse of model of DS is trisomic for a fragment of MMU16 extending from Mrpl39 to 98C21 orf11 (FIG. 3C) that contains at least 132 mouse genes homologous to those present in three copies in DS. Ts65Dn mice recapitulate a variety of DS structural and functional changes. Similar to DS and AD, BFCNs undergo age-dependent degeneration in Ts65Dn mice; this phenotype has been linked to increased gene dose for amyloid precursor protein (App) gene and to a marked decrease in the retrograde transport of nerve growth factor (NGF), the neurotrophic factor for these neurons. In behavioral tests mediated by hippocampus, Ts65Dn mice show significant abnormalities in spacial learning and the ability to recognize novel objects. Given the important modulatory role played by NE-ergic neurotransmission in these tasks and the degeneration of the LC in AD and DS, we asked whether or not the NE-ergic system was impacted in the Ts65Dn mouse.

Using an antibody against tyrosine hyrdoxylase (TH), NE-ergic neurons were examined throughout the rostro-caudal axis of the LC. Unbiased stereology (see Materials and Methods) was used to estimate the total number and cell profile area of TH-immunoreactive (TH-IR) neurons in LC (FIGS. 1B-D & S1A). In 3 month-old mice, there was no significant difference in either parameter. However, at the ages of 6 and 18 months TH-IR cell number was significantly lower in Ts65Dn mice. A similar pattern was observed in the size of TH-IR cell profile areas (FIGS. 1D, S1A). Thus, decreased cell size in Ts65Dn neurons was first detected at 6 months and persisted. The pattern of changes was reminiscent of those documented for BFCNs in Ts65Dn mice. As was true for BFCNs in Ts65Dn, the differences were due both to a decrease in absolute number and to failure to show an increase in number between ages 3 and 6 months, The latter almost certainly reflects decreased TH content in NE-expressing neurons in Ts65Dn mice.

Figure 4:
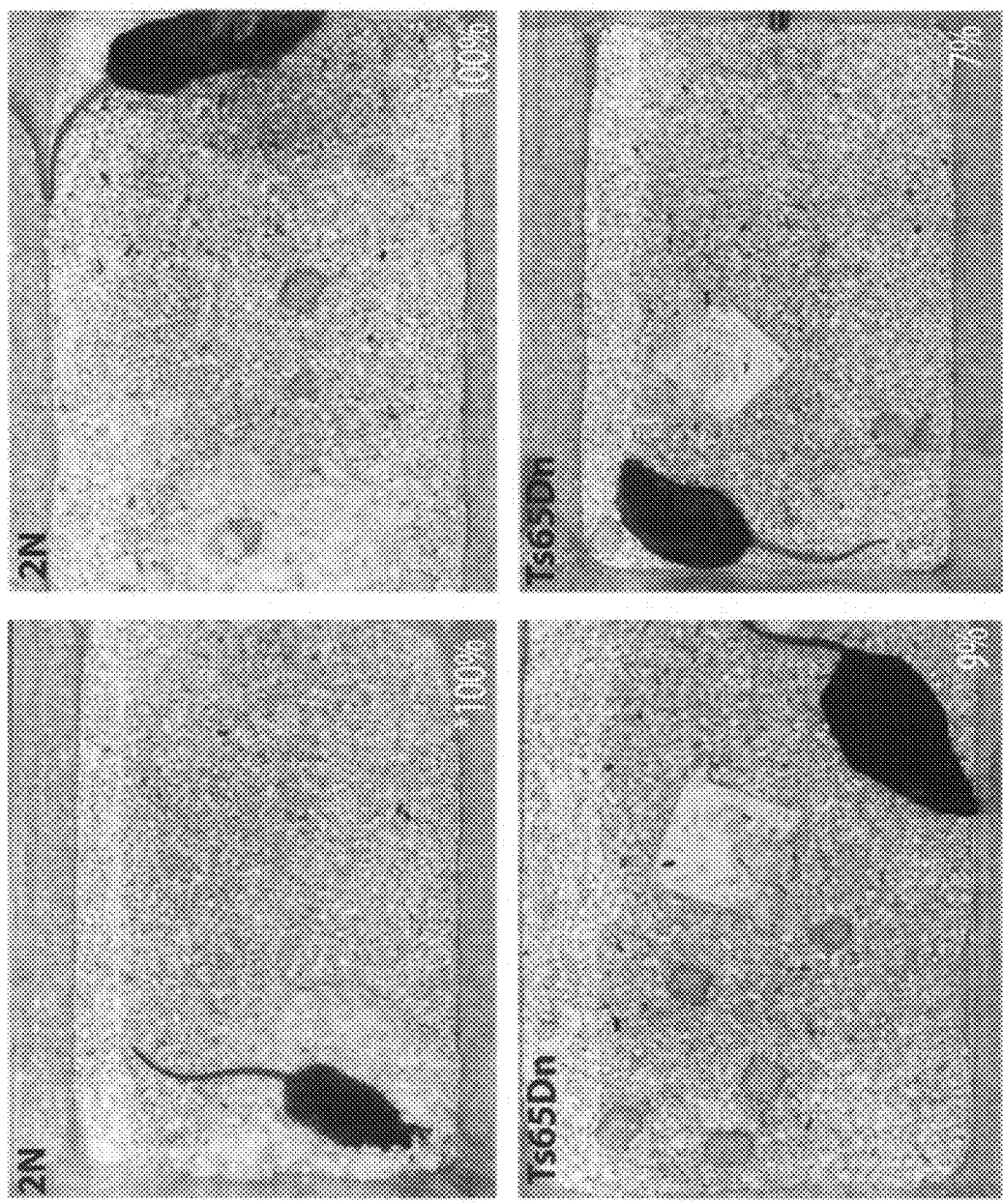
FIG. 4. Photographs showing nesting in 2N and Ts65Dn mice. The amount of nesting material used by each mouse is indicated. 2N mice used a larger percentage of their nesting material compared with Ts65Dn mice.

LC innervates most brain regions; its projections are organized topographically. The anterior pole of LC innervates the hypothalamus while the posterior supplies the HC. The neurons between the poles innervate HC, cerebellum, cortex, and spinal cord (FIG. 4B). We examined the possibility that changes in LC cells would differentiate the different regions of this area. The severity of degeneration in Ts65Dn mice was greatest in the caudal LC (FIG. 4C), a sub-region with extensive projections to the HC. Because LC is the sole source of NE-ergic inputs to HC and neocortex, we examined monoaminergic (MA)-terminals in HC by examining and quantifying staining for vesicular monoamine transporter (VMAT2). A majority of MA-ergic projections to the HC particularly in the DG, are NE-ergic. Comparing Ts65Dn and 2N mice at age 3 months, the DG of Ts65Dn mice showed a significant increase in VMAT2 staining; in particular there was a marked increase in the number of bright puncta (FIG. 5). In contrast, by 6 months, the overall optical density of VMAT2 staining showed an overall decrease of ~20% in comparison to 2N mice (FIG. 1E). These observations are evidence for changes in LC terminals that precede those detected in neuronal somas.

To determine whether or not the morphological change in axon terminals in HC was co related with changes in NE, we examined the levels of this neurotransmitter. There was a significant age-related reduction in NE levels. Comparing the HC in Ts65Dn and 2N mice at 4.5 months of age, there was a 16% reduction in Ts65Dn that was not statistically significant. At 18 months, however, the decrease in Ts65Dn was significant (p=0.0007), averaging 31%. Examining absolute values for NE, there was a decrease with age in both 2N and Ts65Dn mice, but only the change in the Ts65Dn HC was significant (p=0.019; FIG. 1F). These findings gave additional evidence for dysfunction in the terminals of the LC neurons in Ts65Dn mice that preceded those for cell bodies.

Example 2

Figure 6A:
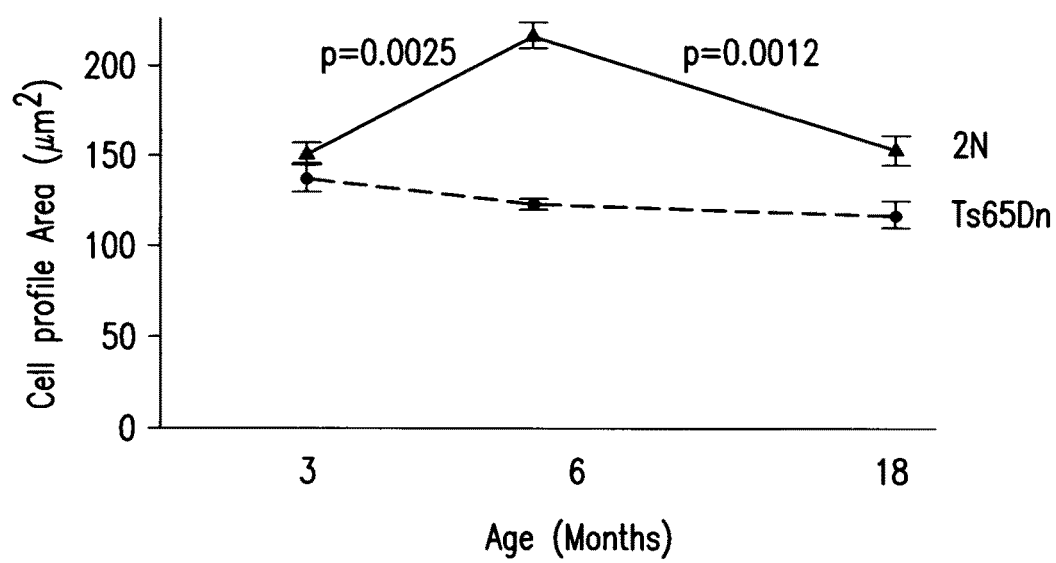
FIG. 6. A) Cell profile area of TH-positive neurons in Ts65Dn and 2N mice in relation to age. Similar to total cell number, there was no significant atrophy of TH-positive neurons in Ts65Dn mice at the age of 3 months (2N=151.6±7, Ts65Dn=139.6±9, p=0.3095). However, there was a significant difference in cell profile area between 2N and Ts65Dn mice at 6 months of age (2N=216.8±7, Ts65Dn=124.4±3, p=0.0006). In very old Ts65Dn mice (18m), there was also a significant atrophy in Ts65Dn mice compared with 2N mice (2N=154.9±8, Ts65Dn=118.3±8, p=0.0140). In relation to the age, unlike Ts65Dn mice, there was a significant increase in cell profile area in 2N mice at 6 months of age compared with 3-month-old mice (p=0.025). Furthermore, 2N mice showed a significant reduction in cell profile area in 18-month-old mice compared with 6-month-old 2N mice. B) Schematic representation of LC projections to cortical and subcortical targets. Different regions of LC project to various brain regions. The rostral part of LC in the rat projects to the hypothalamus. The core of LC projects to hypothalamus, cortex, and spinal cord and the caudal part of LC projects exclusively to the hippocampus (Loughlin et al., 1986). C) Density of TH-Ir neurons across the rostro-caudal axis of LC in 6-month-old 2N and Ts65Dn mice. Although there was a reduction in neuronal density across the rostral-caudal axis of LC, degeneration of TH neurons was more severe in the caudal part of LC. In fact unlike 2N mice, there was a significant reduction in the density of TH-positive neurons in Ts65Dn mice (p=0.045) compared with the rostral region of LC.
Figure 6B:
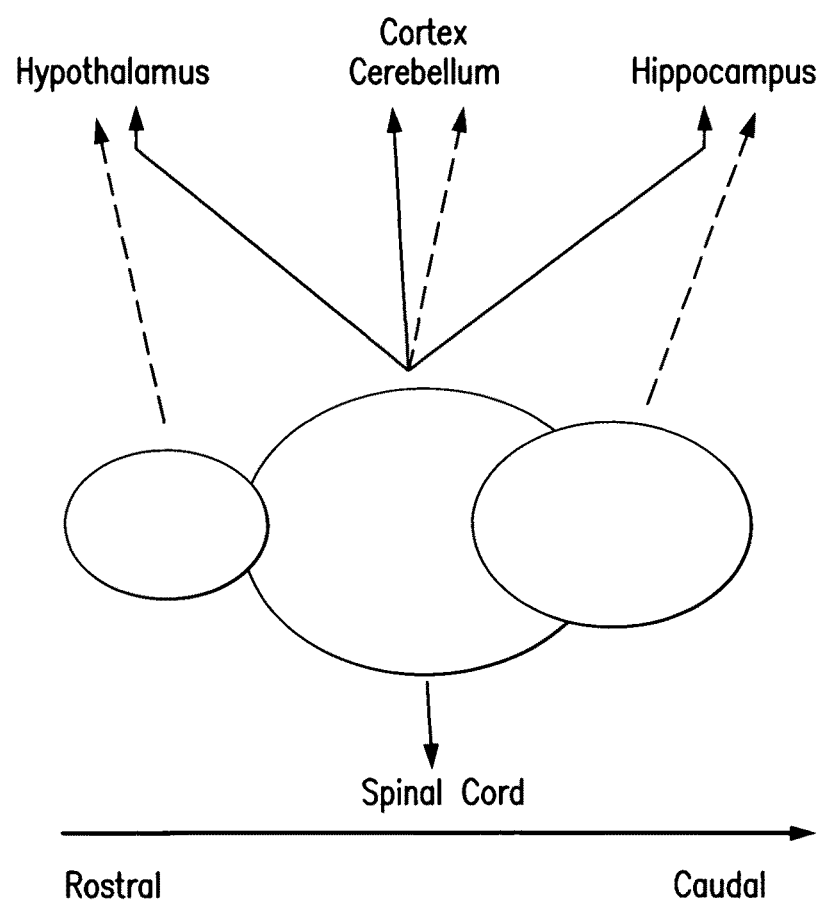
Figure 6C:
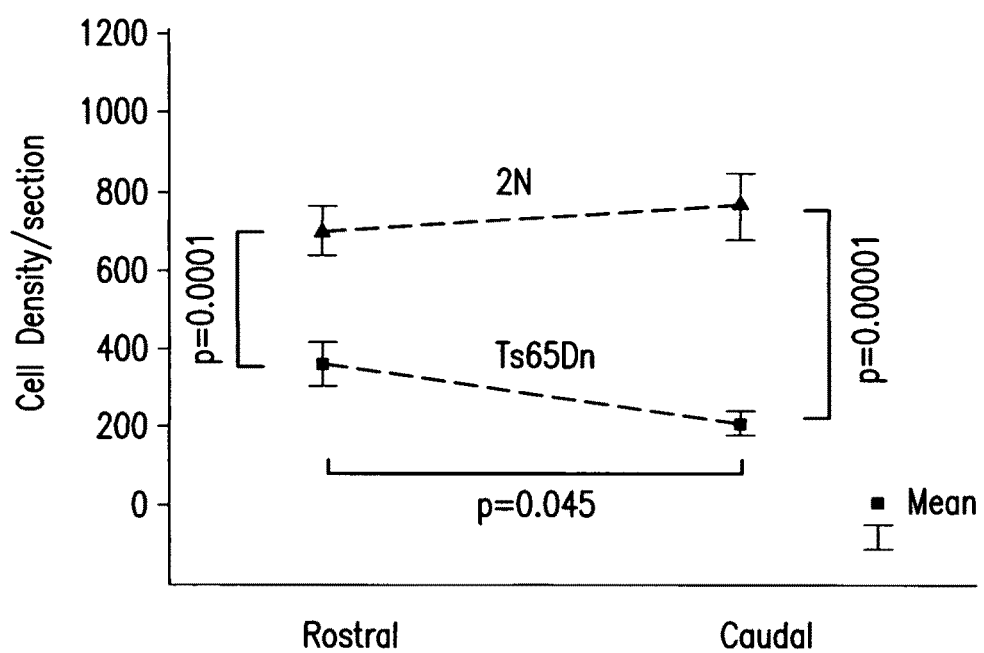

Next, we examined the postsynaptic targets of LC axons in HC. NE-ergic neurotransmission is affected in part through β1-adrenoceptors. The β1 receptor is present on the postsynaptic targets of LC axons in HC and has been shown to play a significant role in cognition, including contextual discrimination. Hippocampal hilar neurons are one locus of β1 adrenoceptor gene expression; immunostaining for these receptors is readily detected on their cell bodies. In Ts65Dn mice at age of 3 months there was a marked increase in the size of β1-Ir cells (FIG. 6). The increase in size was also seen at age 6 months. At 6 months, we also documented a more than 90% increase in the number of β1-Ir neurons in the Ts65Dn HC (p=0.0173; FIG. 2B). At the same time, examining β1-Ir in the entire HC, we also noted an overall increase that was significant. These findings are evidence for changes in the postsynaptic targets of LC neurons, Given the data in Ts65Dn mice for degenerative changes in LC terminals and reduced NE levels, there appears to be a compensatory increase in postsynaptic receptors in response to decreasing NE-ergic transmission.

Example 3

Figure 8B:
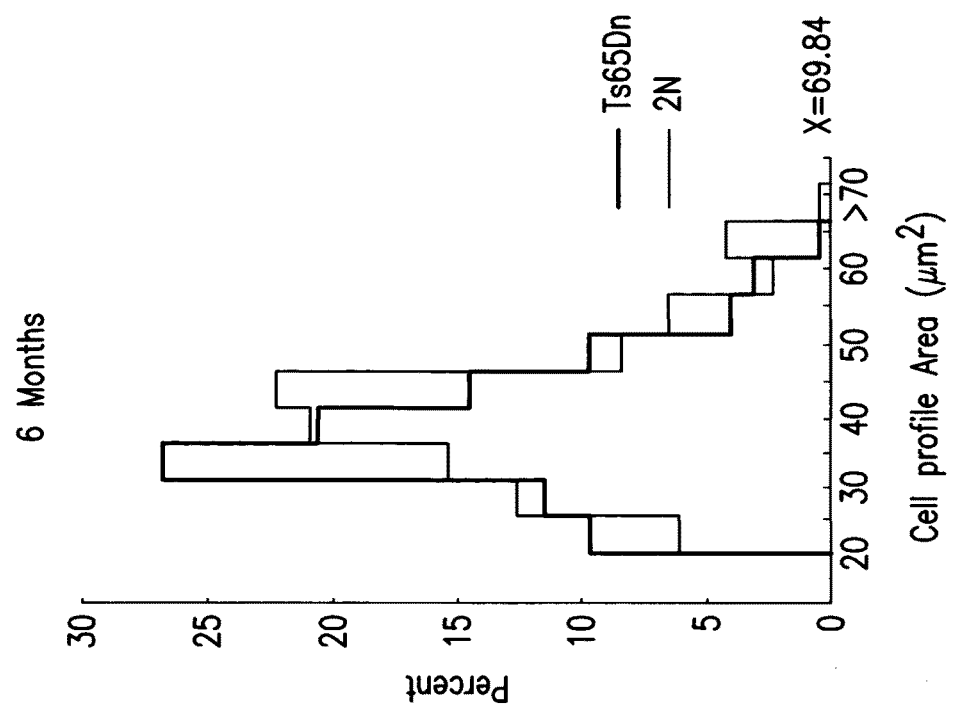
FIG. 8. Frequency distribution of cell profile area of β1-positive neurons in the polymorphic layer of the dentate gyrus in 3 and 6 months old 2N and Ts65Dn mice. At both ages of 3 and 6 months, there was a significant shift to higher values in the frequency distribution of cell profile area in Ts65Dn mice. However, we found the shift to higher values in Ts65Dn mice was stronger in 3 months (X=236.82) than 6 months (X=69.84).
Figure 8A:
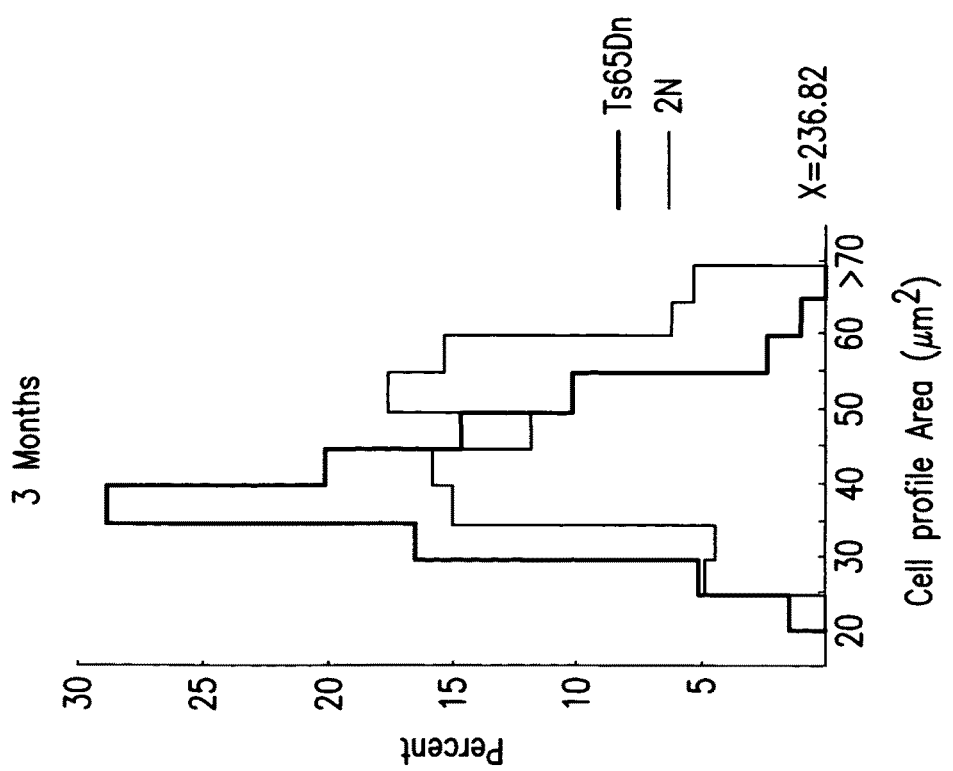
Figure 10B:
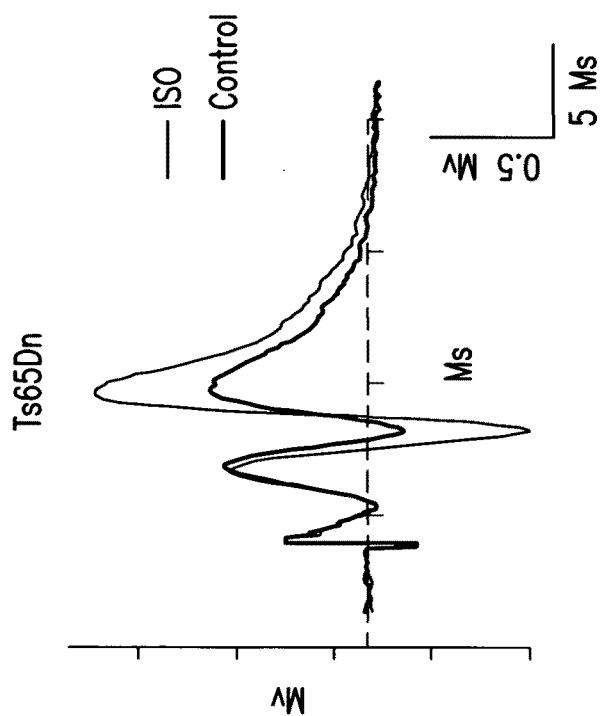
FIG. 10. Recorded responses from the granule cell layer after stimulation of the middle molecular layer before (red) and 30 min after (black line) application of ISO (10 µM, 10 min) in slices of a Ts65Dn (6-month old) and its age-matched 2N control. ISO generated a much stronger response in Ts65Dn than 2N mouse.
Figure 10A:
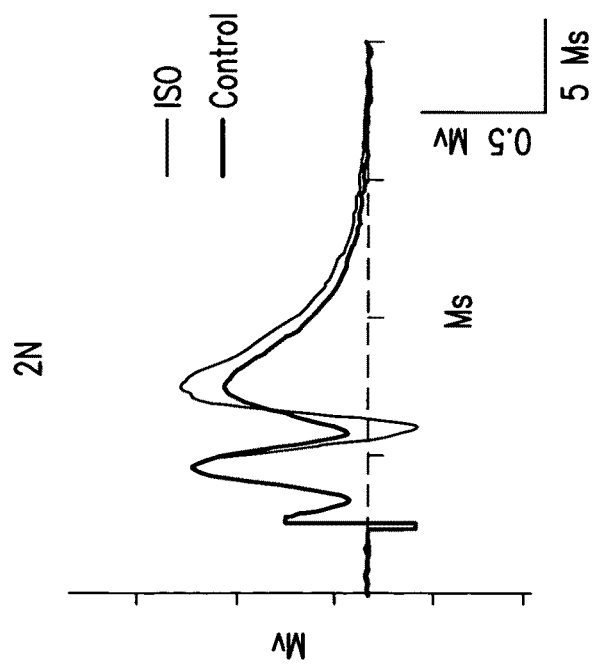
Figure 11A:
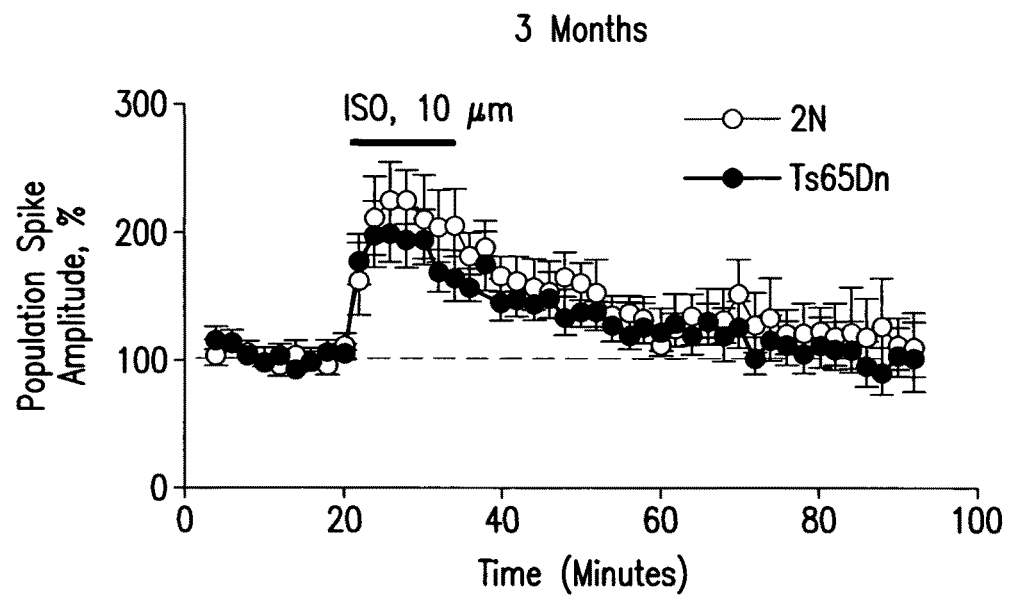
FIG. 11. The effects of releasing (10 µM) ISO in the mid molecular layer of dentate gyrus on changes in population spike amplitude of fEPSPs in 3- and 6-months-old Ts65Dn mice and their 2N controls. In both 2N and Ts65Dn mice and both age groups, ISO generated a significant increase in population spike amplitude of fEPSPs. Application of ISO enhanced the population spike amplitude for at least 30 min in 3-month-old 2N mice. However, in 6 months old mice, the increase lasted more then 1 h.
Figure 11B:
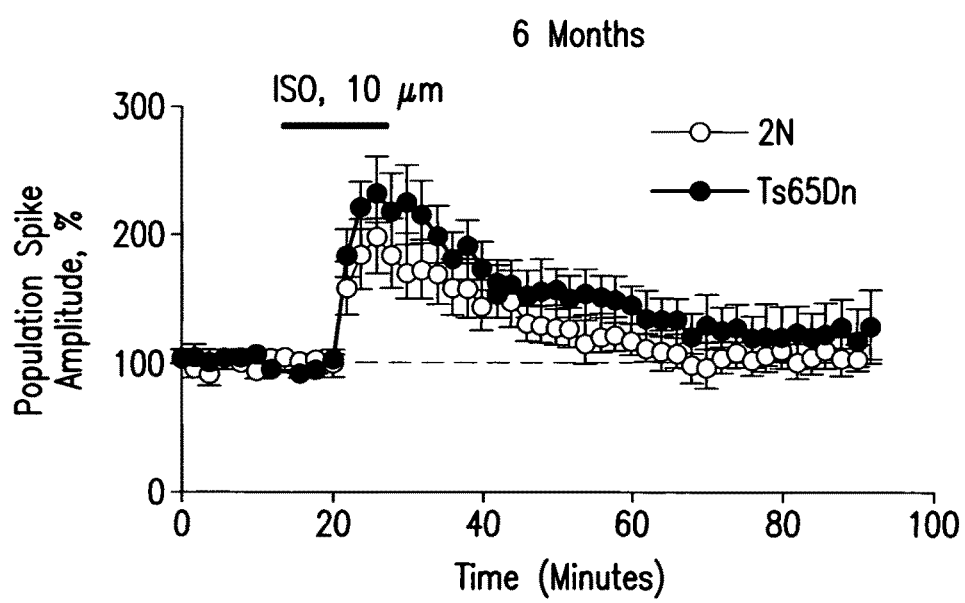

The continued presence of NE receptors on postsynaptic targets raised the possibility that postsynaptic mechanisms activated by NE remained functional even when LC dysfunction and degeneration were advanced. To test whether or not NE signaling would be registered in the DG of Ts65Dn mice, we studied the effect of isoproterenol (ISO), an agonist at both β1 and β2 receptors. For these studies, we applied stimulating current to the middle molecular layer of the DG in acute hippocampal slices, in the absence and presence of ISO, while recording in the DG granule cell layer. In slices taken at age 3 months, there were increase in both the slope and amplitude of excitatory postsynaptic potentials (EPSPs) in both 2N and Ts65Dn mice. The same was true at age 6 months. Remarkably, at age 6 months the responses in Ts65Dn slices were consistently more robust (FIGS. 2A, 8 and 9). These data show that responsiveness to NE is retained following degenerative changes in LC neurons and their terminals in the HC.

To investigate the functional consequences of deficits in LC, we used tests of cued and contextual learning to compare 2N and Ts65Dn mice (FIGS. 2D-F). The contextual fear conditioning test, which registers fear-based responses as episodes of behavioral freezing, differentiates between contextual and cue-based learning. Following training on day 1, mice underwent a test of cued learning on day 2 and contextual learning on day 3. We found no abnormalities in cued learning in Ts65Dn mice (p=0.1825). In contrast, there was a marked failure in Ts65Dn mice in contextual learning (day 3, p=0.0324, FIG. 2D). Indeed, in this test, while 2N mice showed twice as much freezing as was seen on day 1 of testing, in Ts65Dn mice there was no increase.

Nesting behavior is another test that measures hippocampally-based cognition. Prior studies have shown that nesting behavior can be used to define the integrity of hippocampal function. It has been shown to correlate with failed contextual discrimination and spatial learning in rodents. In tests of nesting, mice placed in a novel cage were provided with nesting material in the form of 'nestlets' of known weight (see methods; Fig. S8). Unlike 2N mice, Ts65Dn mice used relatively little of their nestlets (p=0.0012, FIG. 2C) and their nests were poorly formed. These findings are evidence that hippocampal function, and context discrimination in particular, are markedly affected in Ts65Dn mice.

Example 5

Figures 2, 7A:
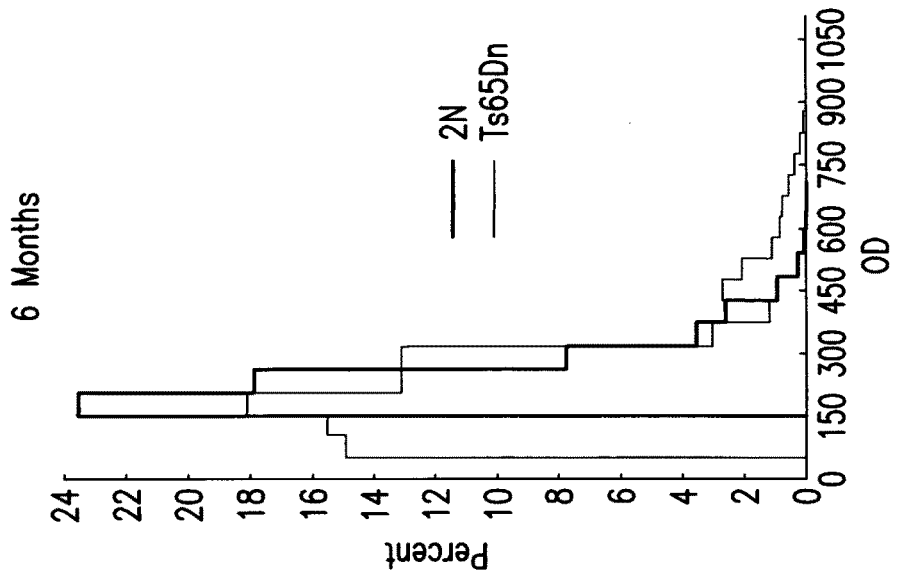
Figures 1, 7A:
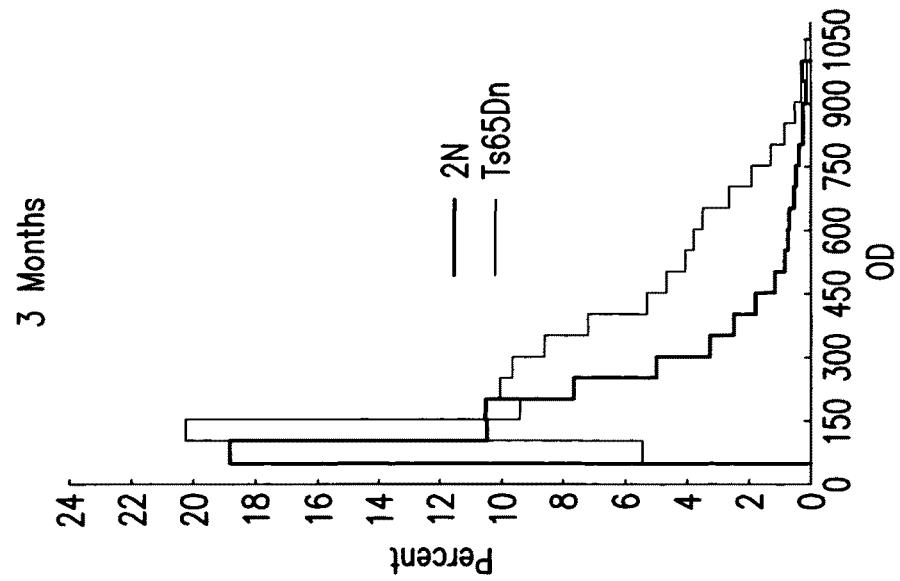
Figure 7B:
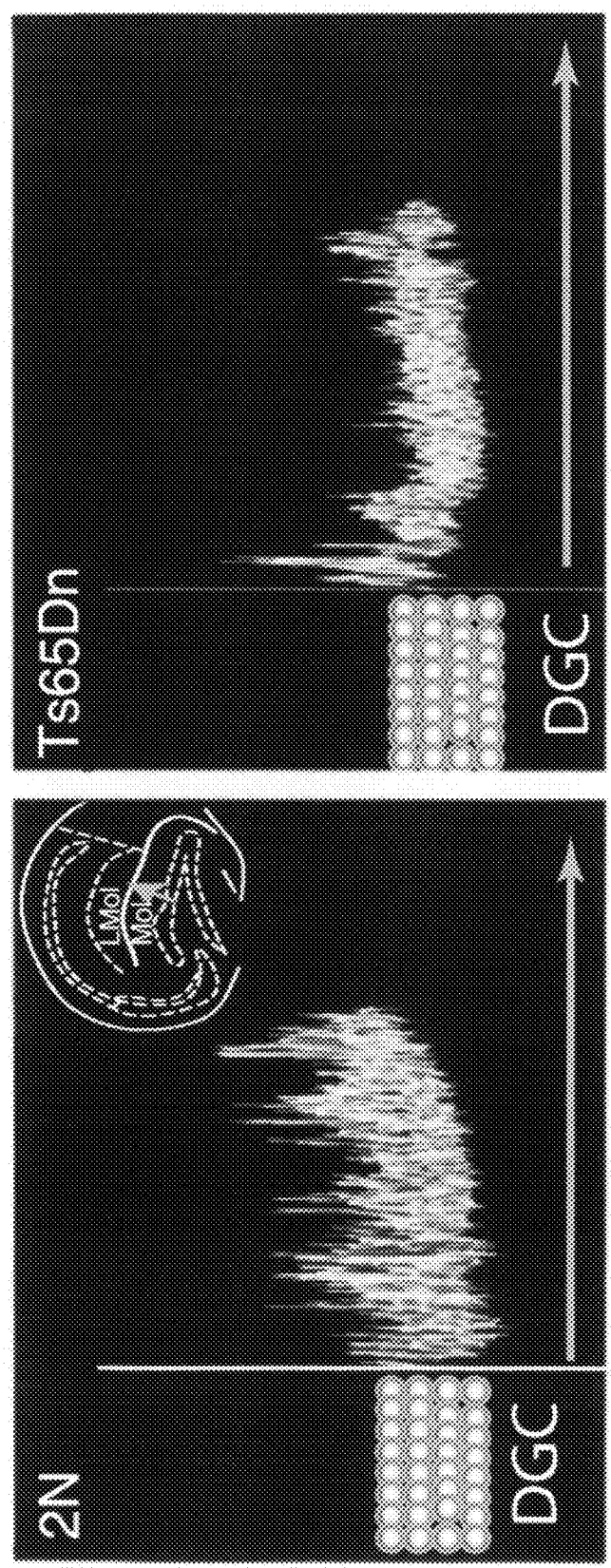
FIG. 7. VMAT2 staining in the inner molecular layer of the dentate gyrus in 3 and 6 month-old mice. A) The optical density was measured in the inner ML and normalized to the optical density of the corpus callosum. At 3 months of age, there was a clear trend toward higher density values in Ts65Dn mice. However, at 6 months of age, there was a significant shift in the frequency distribution of VMAT2 staining to the lower values digits. B) Surface imaging of VMAT2 optical density in the inner ML of DG of a 6-month-old Ts65Dn mouse and its 2N control. The Y axis indicates VMAT2 optical density and X axis depicts the anatomical localization starting from dentate granule cell layer toward the pyramidal cell layer of the hippocampus.

Failure in the contextual component of fear conditioning test and reduced nesting behavior in young Ts65Dn mice suggested a link between LC degeneration and failed learning and memory. To test the idea, we asked if restoring NE levels would rescue contextual fear conditioning in 6 month old mice. An NE prodrug was used that readily crosses the BBB. L-threo-3,4-dihydroxyphenylserine (L-DOPS) or droxidopa is a synthetic amino acid. L-DOPS is metabolized by L-aromatic amino acid decarboxylase within NE-ergic neurons to yield NE. To evoke NE-increases in only the CNS, L-DOPS (1 mg/g) was administered together with carbidopa (CD, 0.125 mg/g), a peripheral DOPA decarboxylase inhibitor that does not cross the blood brain barrier. CD administration alone served as the control. L-DOPS levels were measured six hours after administration in both 2N and Ts65Dn mice. The drug was present in all tissues, including brain, with no difference between genotypes (p=0.4894). The NE levels in the HC of Ts65Dn mice reached to 96% of 2N mice. Because brain NE levels reached maximum levels in brain within 5 hours of subcutaneous administration, mice were tested at this time point. Treatment of 6-month-old Ts65Dn with 20 mg/ml L-DOPS led to a significant improvement in contextual memory (FIG. 2C-F). In the contextual test (day 3), L-DOPS restored fully the difference in freezing between 2N and Ts65Dn mice (FIG. 2D-F, One-way ANOVA p=0.5247). In the control group, in contrast, a significant difference was present (day 3, One-way ANOVA p=0.0002). When performance was measured on a minute-by-minute basis, L-DOPS treatment was associated with increased freezing following the first minute, a pattern shared with 2N mice treated as controls or with L-DOPS. A similar beneficial effect of L-DOPS was found in nesting behavior. Treating young adult Ts65Dn mice and their controls with L-DOPS significantly (p=0.0245) improved nesting in Ts65Dn mice (FIG. 2C). With cessation of treatment, Ts65Dn mice again showed poor nesting behavior (p=0.0121, FIG. 2). These findings are evidence that contextual discrimination can be rescued in mice by increasing tissue levels of NE and provide compelling support for the view that LC dysfunction contributes significantly to failed contextual learning.

Example 6

Increased $\beta$1-adrenoceptor expression raised the possibility that these receptors were involved in transducing th e beneficial effects of L-DOPS in Ts65Dn mice. To test this idea we treated Ts65Dn mice with xamoterol, a $\beta$1-adrenoceptor partial agonist. Comparing Ts65Dn mice and 2N controls treated with either saline or xamoterol during training demonstrated that activation of $\beta$1-adrenoceptors restored failed contextual learning FIG. 3A-B). These findings are evidence that $\beta$1-adrenoceptors play a vital role in mediating the effects of increasing NE-ergic transmission in the Ts65Dn hippocampus. Moreover, by extending the behavioral analysis, these findings show that pharmacologically targeting functionally intact postsynaptic neurons can restore contextual learning.

Example 7

LC degeneration in Ts65Dn mice must be due the action of one or more genes whose dose is increased. One approach to understanding the mechanism of LC degeneration is to identify the gene(s) responsible. To this end we compared mouse models of DS harboring different triplicated fragments of mouse chromosome 16 (MMU16, FIG. 3C). This approach has been use to identify a role for APP in the pathogenesis of BFCN degeneration in Ts65Dn mice. Neither Ts1 Rhr nor Ts1 Cje mice showed significant changes in size or number of LC neurons (FIG. 3D). Consistent with these observations, there was no reduction in VMAT-2 immunostaining at 6 months in Ts1 Rhr mice (FIG. 12). The lack of apparent LC degeneration in Ts1 Cje and Ts1 Rhr mice suggested the responsible gene(s) is located on MMU16 fragment between Gabpa and SodI (FIG. 3C); this region contains about 32 genes, including App. To test whether increased dose for App contributes to LC degeneration, we examined these neurons in Ts65Dn mice bearing either two or three copies of App. Deleting the third copy of App in Ts65Dn mice eliminated the decrease in the size of LC neurons, suggesting that App overexpression is necessary for LC degeneration (FIG. 3E). To ask whether or not App overexpression is sufficient to cause LC degeneration, we examined mice that overexpress a mutant APP transgene. There was a significant decrease in LC neurons in these mice (p=0.0317, FIG. 3F). This latter finding is consistent with a recent report showing degeneration of LC neurons in APP/PS/tg mice. Taken together, the findings are evidence that APP gene dose plays a conspicuous role in the degeneration of LC neurons.

In pursing mechanism(s) by which APP gene dose impacts pathogenesis, it is important to note that the LC appears to be impacted more severely by pathogenic events than their targets of innervation. Indeed, changes in LC axon terminals preceded observed changes in somal size and number, a finding reported also for mouse models of AD. Conceivably, other measures may define all even earlier onset of pathogenesis. In this context it has been shown that Ts65Dn mice at age 2 months fail in tests of contextual discrimination and our ownfindings are consistent with changes in nesting behavior as early as 3 months. In view of the findings for LC in people with DS and those with AD, and the corresponding changes detected in the mouse models of these disorders, a common locus of APP-mediated pathogenesis may well be discovered. We hypothesize that there exists a trophic deficiency whose manifestations arise in the target, a suggestion for which earlier studies provide support. It is possible that local changes in the synthesis or release of a trophic factor or its ability to signal retrogradely are impaired. Of particular interest is the possibility that brain-derived neurotrophic factor (BDNF) may play a role, especially in view of the fact that this protein serves as a trophic factor for both LC neurons.

Herein, we link marked defects in hippocampally-mediated contextual learning in a model of DS to LC dysfunction and demonstrate that these deficits can be restored by treatments targeted at correcting deficient NE-ergic neurotransmission. One important implication of the present invention is that postsynaptic targets of degenerating neurons may remain responsive and functional well after the presence of advanced disease in their presynaptic inputs. If so, treatments that target still functional elements of neuronal circuits can restore circuit function. In particular, treatments targeted to the loss of NE-ergic inputs to hippocampus can enhance cognition in individuals in which these neurons are affected.

Another important aspect of the present invention pertains to the importance of this NE-ergic neurotransmission to contextual learning. It appears that LC modulates the impact of this information on hippocampal function to enhance contextual discrimination. EC gives rise to the medial perforant path (PP) carrying navigational information and the lateral PP conveying sensory information. NE, released by LC, is believed to differentially impact PP inputs. For example, stimulating NE-ergic inputs potentiate the population spike amplitude of the medial PP while depressing synaptic potentials in the lateral PP. The net effect is argued to be an enhanced perception of spacial context. It is noteworthy the NE-ergic inputs also appear to modulate directly or indirectly other neuronal systems with efferents to HC, including cholinergic neurons of the basal forebrain and serotoninergic neurons of the raphe nuclei. Indeed, through NE release from LC axons may play a defining role in cholinergic and serotoninergic neurotransmission. Given the degeneration of these other neuronal systems in the Ts65Dn mouse as well as in DS and AD, it might be argued that dysfunction of the LC represents only one of several deficiencies and that rescuing NE levels would have no effect on cognition. Our data indicates that this is not the case. Rather, the present inventors assert that restoring NE-ergic neurotransmission is effective even in when these other neurons are affected.

In this study, two compounds were tested and found to restore contextual learning. In the case of L-DOPS, the drug is metabolized by LC terminals. In the case of xamoterol, the drug directly accesses receptors. The fact that both compounds were effective suggests that even advanced degenerative changes do not obviate a treatment effect as long as postsynaptic receptors persist. This reinforces the view that restoring NE levels in the hippocampus will act to enhance contextual learning even in patients in which LC degeneration is advanced. Clinical trials to increase NE-ergic neurotransmission in people with DS, and also AD, are expected to show cognitive benefits, To avoid peripheral nervous system activation, trials using drugs whose effects can be targeted specifically to the CNS, as was the case herein for L-DOPS, would be preferred. In this context it is interesting to speculate whether the use of β-adrenergic antagonists with access to the CNS would impair contextual learning. The findings described herein raise concern for the use of such agents in patients with cognitive difficulties involving the LC and hippocampus.

Materials and Methods
Mice Used
a) Ts65Dn Mice

Ts65Dn mice have three copies of a fragment of the mouse chromosome 16 (MMU16) extending from Mrpl39 to 98C21orf11. The Ts65Dn mouse colony was maintained by crossing Ts65Dn females (originally obtained from Jackson Laboratory, Bar Harbor, Me.) to C57BU6JEi×C3H/HeSnJ (B6EiC3Sn) F1 males J (Jackson Laboratory). Genomic DNA isolated from tail was genotyped using multiplex real-time polymerase chain reaction (PCR) with App and ApoB primers to identify 2N and Ts65Dn mice. 3, 4.5, 6, 9, and 18-months old 2N and Ts65Dn mice were used for these studies. All the studies were approved by the Stanford University Committee on Animal Research.

b) Ts1 Cje Mice

Ts1Cje have triplication of a fragment of MMU16 extending from 98C21orf11 to Rac. To generate Ts1Cje mice on a similar genetic background with Ts65Dn mice, Ts1Cje mice on the C57BU6JEi background were crossed with C3H/HeSnJ mice and the resulting Ts1Cje mice were crossed to B6EiC3Sn F1 mice.

c) Ts65Dn:App+/+/− Mice

In order to generate Ts65Dn:App+/+I− mice, Ts65Dn female mice were mated with male mice hemizygous for App, in which App was inactivated by deleting the App promoter. The latter group was kept on the C57BU6JEi×C3H/HeSnJ (B6EiC3Sn) F1 background. As the result, Ts65Dn mice with the three copies of App (Ts65Dn:App+I+/+) and two copies of App (Ts65Dn:App+/+/−) were generated.

d) $APP_{swe}$ and Their Non-tg Littermates

These mice were maintained on a mixed (C3H/HeJ and C57BU6J) background. The $APP_{swe}$ mouse expresses a chimeric mouse/human APP695 containing the human Aβ domain and mutations (K595N, M596L) linked to familial AD.

Immunocytochemistry

Histological analyses were performed blind to genotype. LC neurons were identified by immunocytochemical staining for tyrosine hydroxylase (TH). TH is a rate-limiting enzyme converting L-tyrosine to dihydroxyphenylalanine (DOPA). TH is widely used as a marker for catecholaminergic neurons particularly NE-ergic neurons in LC. A polyclonal antibody (Protos Biotech Co., New York) was used to label TH-positive neurons. The brain of Ts65Dn, Ts1Cje, and 2N mice was examined at 3, 6, and 18 months of age. The cell bodies of LC were examined at each age. Mice were deeply anesthetized with sodium pentobarbital (200 mg/kg i.p., Fort Dodge Animal Health, Fort Dodge, Iowa) and perfused for subsequent immunocytochemical detection of TH (1:2,000) in 70 μm free-floating coronal sections through brain stem and HC. For each group of mice, identical conditions were used. Unbiased stereological methods (Stereologer, Systems Planning & Analysis, Alexandria, Va.) were used to determine the number (optical fractionator method) of TH-positive neurons throughout the rostral-caudal extent of LC of each animal. The cross-sectional areas of TH-positive neurons randomly sampled throughout the rostral-caudal extent of LC was also determined using an Image Pro Plus (Bethesda, Md.). To study MA-ergic terminals, a polyclonal antibody against mouse vesicular monoamine transporter (VMAT2, Phoenix Pharm. Inc, Belmont, Calif.) was used in the coronal sections through the HC. VMATs are members of a family of trans-membrane carriers on synaptic vesicles. VMAT2 is an isoform of VMAT1, which is exclusively found in catecholaminergic neurons (7). For TH: 3 months (2N=5, Ts65Dn=5), 6 months (2N=9, Ts65Dn=7) and 18 months (2N=6, Ts65Dn=7, Ts1Cje=5, $APP_{swe}$=5, WT=5), for β1-adrenoceptor: 6 months (2N=6, Ts65Dn=5) and for VMAT2: 3 months (2N=5, Ts65Dn=5) and 6 months (2N=4, Ts65Dn=3) mice were used.

Behavioral Studies
1) Fear Conditioning

Contextual and tone-cued fear conditioning tests were performed using the Fear Conditioning Video Tracking System (Med-Associates Inc., St. Albans, Vt.). To reduce the stress, each mouse was handled for 5 days. After that, the mice underwent three days of Training day, Tone-Cued in novel context testing day, and Contextual testing day. In the first day, mice went through the Training session. Prior to conditioning, each mice had 3 min to explore the Test Chamber (baseline activity and then they received five tone-shock pairings). The shock (0.5 mA, 50 Hz, 2 sec) delivered after 18 sec from the end of the tone (70 dB, 2 kHz, 20 sec). Therefore, an empty trace interval interposed between the tone and the shock in each conditional stimulus-unconditional stimulus pairing. On the second day (Tone-cued testing day), mice were placed in the novel context (new olfactory and visual cues) for 3 min and subsequently were presented three tone presentations (same as the Training Day) without any shocks. On the last day of the experiment, mice were placed in the context similar to the Training Day for 5 min without any tones or shocks.

a) Effects of L-DOPS on Fear Conditioning

The effect of L-DOPS on fear conditioning was investigated by treating Ts65Dn mice and their controls 5 hours before the start of each test. The treated mice underwent three days of Training day, Cued testing day and Contextual testing day. L-DOPS was diluted (20 mg/ml) in 0.2M HCL containing 2 mg/ml ascorbic acid. The pH was neutralized with 10M NAOH just before the injection. To counter the peripheral effects of L-DOPS, S-(–) carbidopa was used. Carbidopa was diluted in the same solution (2.5 mg/ml) as L-DOPS. Two groups (10 pairs each) of 5-6-month-old male Ts65Dn and 2N mice were either injected with carbidopa (2.5 mg/ml) or a combination of 20 mg/ml L-DOPS and 2.5 mg/ml carbidopa (50 μl/g subcutaneously) five hours before the start in all 3 days of the experiment. Six-months-old 2N (CD=13, CD+L-DOpS=11) and Ts65Dn (CD=10, CD+L-DOPS=9) mice were used for this study.

b) Effects of Xamoterol on Fear Conditioning

The effect of β1-partial agonist (xamoterol) on Ts65Dn mice and their controls 1 hours before fear conditioning was investigated by treating the start of each test. Xamoterol hemifumarate (Tocris Bioscience, Ellisville, Mich.) was freshly diluted in saline. Two groups of 9-month-old (19 2N and 15 Ts65Dn) mice were subcutaneously injected either with xamoterol (3 mg/kg) or saline (10 ml/kg) exactly t hour before all 3 days of fear conditioning test. Nine-months-old 2N (saline=4, xamoterol=8), and Ts65Dn (saline=4, xamoterol=6) mice were used for this study.

Statistical Methods for Behavioral Testing

The data tested using one-way analysis of variance (ANOVA) between the genotypes. The significance of genotype and treatment effects was confirmed by a non-parametric Mann-Whitney U-tests.

2) Nesting Behavior Analysis

The nesting experiment was performed using 10 pairs of 6-month-old male Ts65Dn (CD=10, CD+L-DOPS=10) and 2N (CD=10, CD+L-DOPS=10) mice. The nesting behavior was analyzed in three different periods (sham, drug and no treatment):

Sham Period

Each mouse was placed in individual mouse cages for 4 days. On day 5, each mouse was injected subcutaneously at 1 PM with 50 μl/g of (2.5 mg/ml) carbidopa (Sigma) and returned to their individual cages. The next day, mice were injected the same amount of carbidopa as the day before at 1 PM. At 6 PM, the mice were transferred to a rat cage and one nestlet was placed in each cage. Next morning, the nesting was scored by three investigators blind to the genotype. This was followed by weighing the remaining nestlets.

Drug Period

Following the sham experiment, mice were returned to their individual mouse cages without any nestlets for 6 days. On day 7, the mice were injected subcutaneously (50 μl/g) of a combination of (20 mg/ml) L-DOPS and carbidopa (2.5 mg/ml) at 1 PM and were returned to their individual mouse cages. Next day the injection was repeated at 1 PM and at 6 PM the mice were transferred to clean rat cage with one nestlet. The quality and quantity of nesting was scored the morning after.

No Treatment (Washout) Period

The mice were kept in individual cages for two weeks to minimize the effects of L-DOPS treatment on nesting. At the end of this period, each mouse was transferred to a rat cage and was exposed to one nestlet. The quality and quantity of nesting was scored the morning after.

Norepinephrine and L-DOPS Determination a) Tissue Preparation

Mice were deeply anesthetized using sodium pentobarbital (200 mg/kg i.p.) and brains were extracted immediately. The right hippocampal region dissected out on ice, weighed, and frozen shortly after. The rest of the right hemisphere was also weighed and collected. For homogenization, 1 ml of ice-cold 0.05 M phosphoric acid (Sigma) with 10 μl of 110 μl/ml of 3,4-Dihydrxybenzylamine hydrobromide (DHBA; Sigma) used as an internal standard. The tissue samples were sonicated for 3 seconds on ice. The resulting homogenates were centrifuged at 15,000 g for 15 minutes at 4° C. The resulting supernatant was transferred to a conical tube containing 1 ml of 3M tris (pH: 8.6) with 90 mg acid-washed aluminum oxide (Sigma). The mixture was rotated at 4° C. overnight. The alumina was centrifuged for 10 seconds, and washed briefly with 6 mM tris (pH: 8.6) and 3 changes of water (HPLC grade). After final centrifugation, the resulting precipitate was mixed with 1.8 ml of 0.05M $H_3PO_4$ (Sigma, puriss>99%) for 30 minutes at 4° C. The solution was filtered with a 0.2 μm filter and used for UV-based HPLC. 4.5 months-old (N=4 pairs of 2N and Ts65Dn) and 18 months (2N; N=8 and Ts65Dn; N=6) were used for this study.

b) HPLC Method

A UV-HPLC machine (Varian, Chicago) equipped with an auto sampler and 2 pumps was used for this study. The machine was connected to a Varian column (Pursuit PFP, 150 mm×4.6 mm, 5 μm, A3050150×046) optimized for catecholamine measurements in aqueous conditions. The mobile phase was consisted of 60% 0.1M citric acid (Sigma) and 40% 0.1M $Na_2HPO_4$ both in 0.3 mM HPLC-grade sodium octyl sulfate salt (Sigma) (7). The mobile phase was degassed using 0.2 μm filter and refreshed every week. The flow rate was set at 1.0 ml/min at room temperature and the detection was performed at 270 nm. To achieve maximum performance, the mobile phase was pumped at 0.1 ml/min flow the night before the experiment. The column was washed thoroughly with 50% methanol after each experiment. To calculate the amounts of catecholamines, the height of the peak generated by DHBA, NE, and L-DOPS were measured using Variant software. The following formula was used to calculate the amounts of NE and LDOPS per g tissue:

ng NE per gram tissue=[(peak height NE/peak height DHBA) *(ng DHBA added to the tissue)*(peak height per ng DHBA/peak height per ng NE)]/tissue weight (grams). For standardizations, we used DHBA (Sigma), NE (hydrochloric salt, Sigma) and L-DOPS. Prior to these experiments, a very significant linear correlation between the DHBA, NE and L-DOPS peak height(s) ($p<0.00001$) and the concentration was established.

Electrophysiological Recordings

Three and 6-month-old 2N and Ts65Dn mice were anesthetized with isoflurane before decapitation. The brain was quickly removed and immersed for 2-3 min in ice-cold artificial CSF (ACSF) [containing (in mM): 119 NaCl, 2.5 Kcl, 2.5 $CaCl_2$, 1.3 $MgSO_4$, 1 $NaH_2PO_4$, 26 $NaHCO_3$, and 10 glucose], osmolarity 310, continuously bubbled with 95% O2 and 5% $CO_2$, pH 7.4. The HC was extracted and cut in ice-cold ACSF with a vibratome (Leica 1000; Leica, Nussloch, Germany) into 350-μm-thick transverse slices, which were allowed to recover in oxygenated ACSF at 32° C. for 30 min, and then at room temperature for an additional 1-10 hr before experimental recordings.

b) Recording of Evoked Field Potentials

Slices were transferred into the recording chamber and superfused with ACSF at a constant rate of 2.5 ml/min at a temperature of 32° C. Recording electrodes were made of borosilicate glass capillaries (1B150F, World Precision Instruments, Sarasota, Fla.) and were filled with 2M NaCl (resistance 0.3-0.5 mg-2). Mono polar stimulating electrode was maid of Pt/Ir wires with diameter 25.4 μm (PTT0110, World Precision Instruments, Sarasota, Fla.) and had 100-μm-long exposed tip. The stimulating electrode was inserted under visual control perpendicular to the slice surface into the middle molecular layer (MML), and the recording electrode into the granule cell layer of the DG upper blade. The distance between the electrodes was 250-300 µm. Testing stimuli evoked field responses with population spike amplitudes 65-75% of maximum. The amplitude of the population spike was measured as follows: a line was drawn at the base of the population spike connecting the first and second peaks of the field response, a second line was drawn at the peak of the population spike (i.e., at the peak of the downward deflection), and at the peak of the spike, a line was drawn vertically between these two lines, thus giving the amplitude of the population spike. The magnitude of the fEPSP was measured as the initial slope of the linear part of the fEPSP, which occurred 0.1-1 ms after the presynaptic volley. After stabilization of evoked responses and at least 30 min of stable recordings, an agonist of adrenergic β1 and β2 receptors isoproterenol (1 µM) was bath applied for 10 min.

Without treatment, the Ts65Dn mouse models of DS remembered 44% less than their controls. However, after the treatment with L-DOPS, mouse models of DS remembered only 8% less than their controls. This suggests that the deficiency in Ts65Dn mice was reduced by 80% (FIG. 1B).

We have demonstrated that L-DOPS are able to alleviate cognitive failure in mouse models of DS. Based on the literature, L-DOPS has been used safely up to 1 gram per day in humans.

Down syndrome (DS) causes marked deficits in contextual learning and memory. In rodents, these tasks are hippocampally-based and mediated by norepinephrine-ergic locus coeruleus (LC) afferents. To explore the basis for contextual learning defects in DS, we examined the Ts65Dn mouse model. There were significant deficits in contextual learning together with dysfunction and degeneration of LC neurons. However, the postsynaptic targets of innervation remained responsive to noradrenergic receptors agonists. Indeed, in spite of advanced LC degeneration, contextual learning failure was reversed using either L-DOPS, a prodrug for NE, or xamoterol, a β1-adrenoceptor partial agonist. Increased gene dose for App was necessary and sufficient for LC degeneration. Our findings raise the possibility that restoring NE-ergic transmission or reducing APP levels would reverse cognitive dysfunction in DS.

In pursuing mechanism(s) by which App gene dose impacts pathogenesis, it will be important to note that the LC appears to be impacted more severely by pathogenic events than their targets of innervation. Indeed, changes in LC axon terminals preceded observed changes in soma size and number, a finding reported also for mouse models of AD. Conceivably, other measures may define an even earlier onset of pathogenesis. In this context it has been shown that Ts65Dn mice at age 2 months fail in tests of contextual discrimination and our own findings are consistent with changes in nesting behavior as early as 3 months (Colas et al, In preparation). In view of the findings for LC in people with DS and those with AD, and the corresponding changes detected in the mouse models of these disorders, it is possible that LC dysfunction contributes to cognitive changes in both children and adults. What mechanism is responsible for APPmediated pathogenesis is yet to be discovered. As one possibility, there may exist a trophic deficiency whose manifestations arise in the target, a suggestion for which earlier studies provide support. It is possible that local changes in the synthesis or release of a trophic factor or its ability to signal retrogradely are impaired. Of particular interest is the possibility that brain-derived neurotrophic factor (BDNF) may play a role, especially in view of the fact that this protein serves as a trophic factor for LC neurons.

Herein, we link marked defects in hippocampally-mediated contextual learning in a model of DS to LC dysfunction and demonstrate that these deficits can be restored by treatments targeted at correcting deficient NE-ergic neurotransmission. The most important implication of the work is that postsynaptic targets of degenerating neurons may remain responsive and functional well after the presence of advanced disease in their presynaptic inputs. If so, treatments that target still functional elements of neuronal circuits may restore circuit function. In particular, it can be suggested that treatments targeted to tire loss of NE-ergic inputs to hippocampus may prove effective in enhancing cognition in people in which these neurons are affected.

Our findings point again to the importance of this NE-ergic neurotransmission to contextual learning. It appears that LC modulates the impact of this information on hippocampal function to enhance contextual discrimination. EC gives rise to the medial perforant path (PP) carrying navigational information and the lateral PP conveying sensory information. NE, released by LC, is believed to differentially impact PP inputs. For example, stimulating NE-ergic inputs is being shown to potentiate the population spike amplitude of the medial PP while depressing synaptic potentials in the lateral PP. The net effect is argued to be an enhanced perception of spatial context. It is noteworthy that NE-ergic inputs also appear to modulate directly or indirectly other neuronal systems with efferents to HC, including cholinergic neurons of the basal forebrain and serotoninergic neurons of the raphe nuclei. Indeed, through NE release from LC axons may play a defining role in cholinergic and serotoninergic neurotransmission. Given the degeneration of these other neuronal systems in the Ts65Dn mouse as well as in DS and AD, it might be argued that dysfunction of the LC represents only one of several deficiencies and that rescuing NE levels would have no effect on cognition. Our data argue that this is not the case. They indicate that restoring NE-ergic neurotransmission is effective even in when these other neurons are affected.

In this study, two agents acted to restore contextual learning. In case of L-DOPS, the drug is metabolized by LC terminals. In the case of xamoterol, the drug would directly access NE receptors. The fact that both agents were effective suggests that receptor activation is functioning, thus reflecting the need for neuronal LC axonal terminals. By extending the analysis to humans, restoring NE levels in the hippocampus may act to enhance contextual learning even in patients in which LC degeneration is advanced. Future trials to increase NE-ergic neurotransmission in people with DS, and possibly AD, may show cognitive benefits. To avoid peripheral nervous system activation, trials using drugs whose effects can be targeted specifically to the CNS, as was the case herein for L DOPS, would be preferred. In this context it is interesting to speculate that the use of β-adrenergic antagonists with access to the CNS might impair contextual learning. Our findings raise concern for the use of such agents in patients with cognitive difficulties involving the LC and HC.

In addition to DS, any diseases or conditions that are associated with LC degeneration may be treated to improve patient cognitive ability in accordance with the present invention. Theoretically, the use of L-DOPS would be beneficial in AD, Parkinson's disease, Huntington's disease, dementia pugilistica, and Wernicke-Korsakov syndrome.

For example, there are a number of similarities between AD and DS.

- Both mouse modes of DS (Ts65Dn) and AD (T92576) show failed contextual learning.
- Our submitted study shows that LC undergoes degeneration on both mouse models of DS (Ts65Dn) and AD (APPswe).

Every DS patient will eventually show Alzheimer brain pathology after the age of 40.

Mutations in APP gene always lead to the familial form of AD. Interestingly, the triplication of APP gene is necessary for the appearance of AD pathology in people with DS.

The hippocampus, which plays a critical role in contextual learning, is affected in both AD and DS. However, the amygdala which is involved in cued recall is usually spared in both disorders. LC undergoes severe degeneration in both AD and DS.

All aspects of the present invention as described above are contemplated as being used to improve cognitive dysfunction in mammals, in general, exhibiting a degeneration of LC. For examples, while mice, rats, rabbits and even cats may be mentioned for their use in research, it is particularly contemplated that the present invention will be especially advantageous in improving cognitive ability in humans in clinical settings, where the humans exhibit a disease or condition which lead to a degeneration of LC.

Further, in accordance with the present invention although it is preferred to use either L-threo-DOPS or (+)-erthyro-DOPS, it is also acceptable to use a racemic mixture (50/50) of D- and L-threo-DOPS. If the racemic mixture is used, higher doses may be used.

Generally, amount of from about 50 μg to about 800 μ/kg of body weight of either L-threo-DOPS or (+)-erthyro-DOPS is administered. Preferably, from about 150 μg to 600 μg/kg of body weight is administered. However, higher amounts may be used provided that the amount used is well below the $LD_{50}$ value. If a racemic mixture of D- and L-threo-DOPS is used, higher amounts, such as from about 200 μg to about 1 μg/kg of body weight is used.

More generally, the dosages described above may be used with any of the compounds administered with any of the methods disclosed herein. The dosages may be administered once per day for a period of from one day to several weeks, and may be increased or decreased in accordance with the treating physician or veterinarian.

Any such mode of administration may be used, such as orally, parenterally or even sub-cutaneously. As examples of carriers or excipients which may be used to administer suitable compositions, U.S. Pat. No. 4,330,558 is noted, which is incorporated herein the entirety. It is preferred, however, if the mode of administration is parenteral.

Furthermore, in accordance with the present invention, it is specifically contemplated that norepinephrine reuptake inhibitors (NRIs) be used to increase HC levels of NE.

Examples of NRIs that may be used include selective NRIs, such as atomoxetine, mazindol, nisoxetine, reboxetine and viloxazine. However, other strong NRIs, such as (R)-thionisoxetine and clomipramine may be used in accordance with the present invention. All of these compounds are known and preparatory methods therefor are described in U.S. Pat. No. 6,541,668 (atomoxetine); U.S. Pat. No. 7,473,804 (atomoxetine); U.S. Pat. No. 5,217,987 (mazindol); U.S. Pat. No. 5,447,948 (mazindol); U.S. Pat. No. 6,376,711 (nisoxetine); U.S. Pat. No. 6,391,876 (reboxetine); U.S. Pat. No. 4,229,449 (reboxetine); U.S. Pat. No. 4,782,054 (viloxazine); U.S. Pat. No. 5,281,624 ((R)-thionisoxetine) and U.S. Pat. No. 6,495,154 (clomipramine), each and all of which patents are incorporated by references herein the entirety. The dosages recited above may be used for any of these additionally disclosed compounds as well.

Further, the esters, diesters or trimesters of NE, and particularly the natural isomer, L-(−)-(R)-NE, may be readily prepared by well known esterification reactions (and methods using the same) of NE, and the natural isomer. NE and its natural isomer are readily available from biochemical and specialty supply companies. To counter the peripheral effects of NE, an FDA-approved β1 receptor selective antagonist (atenolol) which does not cross the BBB will be simultaneously used (oral dose of 25 to 100 mg).

The present invention, thus, provides several methods based upon the above disclosure. First, a method of treating an individual having DS is provided, which entails administering an amount of one or more compounds or pharmaceutically-acceptable salts thereof to the individual, which improve cognitive functioning in the individual by increasing hippocampal NE levels. The one or more compounds or pharmaceutically-acceptable salts thereof are an NE prodrug or a Beta 1-adrenoreceptor agonist or the phosphate, sulfate, chloride, acetate or citrate salts thereof, for example. However, any pharmaceutically-acceptable salt may be used.

The NE prodrug is preferably L-threo-3,4-dihydroxyphenylserine (L-DOPS) or a monoester, diester or triester thereof which may be hydrolyzed in vivo to release NE. The mono-, di- or tri-esters are preferably lower alkyl, i.e., C1-C6, esters.

Further, the NE prodrug is preferably converted in vivo to NE within NE-ergic neurons. Also, it is preferred that the one or more compounds or salts thereof used evoke NE increases in the central nervous system, but not the peripheral nervous system, and that they target functionally intact postsynaptic neurons. Moreover, it is preferred that the one or more compounds or salts thereof at least partially correct deficient NE-ergic transmission.

Most preferably, the at least partial correction of deficient NE-ergic transmission is effected by activation of β1-adrenoreceptors.

Additionally, it is most preferred that the at least one or more compounds or salts thereof do not increase levels of L-DOPA or dopamine upon administration, and that they also function as NE reuptake inhibitors.

Second, the present invention also provides a method of stimulating postsynaptic targets of degenerating neurons in an individual having a disease or impaired condition of the presynaptic inputs thereof, which entails administering an amount of one or more compounds which stimulate the postsynaptic targets of the degenerating neurons, whereby the individual exhibits an improved cognitive ability.

The one or more compounds or pharmaceutically-acceptable salts thereof are an NE prodrug or an NE uptake inhibitor.

Third, a method of improving contextual learning in an individual having a disease or condition causing impaired contextual learning is provided, which entails administering one or more compounds or salts thereof which at least partially restore deficient NE-ergic transmission.

Preferably, the one or more compounds or salts thereof stimulate postsynaptic targets of degenerating neurons, and are an NE prodrug.

Preferably, the disease or condition treated is DS, AD or Wernicke-Korsakoff syndrome.

It is also preferred that the at least partial restoration of deficient NE-ergic transmission is effected by activation of β1-adrenoreceptors, and that the one or more compounds or salts thereof do not increase levels of L-DOPA or dopamine upon administration.

Most preferably, one compound or a salt thereof is administered, which is L-DOPS.

Fourth, a method of increasing cognitive ability in an individual exhibiting cognitive impairment is provided, which entails administering one or more compounds that are either metabolized by LC terminals or LC receptors or both, thereby increasing NE-ergic transmission.

Preferably, the cognitive impairment is caused by DS or AD. The one or more compounds or salts thereof are either an NE prodrug or a β1-adrenoreceptpr agonist. The one or more compounds or salts thereof may also be an NE reuptake inhibitor. Preferably, one compound or salt thereof is used, which is L-DOPS.

Fifth, a method of treating defective hippocampally-mediated contextual learning and improving cognitive ability in an individual is provided, which entails administering one or more compounds or salts thereof that are either metabolized by LC terminals or LC receptors or both.

The one or more compounds or salts thereof used may be an NE prodrug or β1-adrenoreceptor, or even an NE reuptake inhibitor.

Preferably, the defective hippocampally-mediated contextual learning is caused by DS or by a disease or condition exhibiting degeneration of LC. Also, it is preferred that the one or more compounds or salts thereof used do not increase levels of dopamine or L-DOPA upon administration. Most preferably, one compound or salt thereof is used, which is L-DOPS.

The effectiveness of the present invention in treating AD has been corroborated by Heneka et al as reported at PNAS, vol. 107, no. 13, 6058-6063, Mar. 30, 2010. In more detail, it has now been demonstrated that chronic NE depletion in APP-transgenic mice increases the degree of neuroinflammation in areas usually innervated by LC. This finding suggests that the early degeneration of LC neurons and their terminals, which result first in a local, and then an overall NE deficiency, may facilitate the inflammatory reaction in response to Aβ deposition in the AD brain. That is, NE deficits may directly contribute to early neuronal dysfunction by subsequent elevation of inflammatory molecules. Further, the data provided in the PNAS paper of Heneka et al, suggests that NE acts, beyond its role as a neurotransmitter, as an important regulator of microglial functions facilitating Aβ clearance. Perhaps, most importantly, given that NE suppresses brain inflammation and enhances Aβ phagocystosis at the same time, restoration of brain NE levels may be expected to exert a desirable effect and provide a vaccination strategy for AD.

Thus, the present invention also provides a method of suppressing brain inflammation by restoring brain NE levels, including hippocampal levels, which entails administering one or more NE prodrugs or a β1 adrenoreceptor agonist. Any of the aforementioned NE prodrugs or β1 adrenoreceptor agonists in this specification may be used in this particular method and in the same ranges of amounts and modes of administration noted above. Preferably, an NE prodrug is used and which is L-threo-3,4-dihydroxyphenylserine (L-DOPS). This method was also be used in conjunction with NRI administration in the same manner as described above.

Finally, all of the compounds or salts thereof described herein may be obtained commercially or produced using well known methodologies. For example, L-DOPS and threo-DOPS may be produced using any of the methodologies disclosed in U.S. Pat. Nos. 4,562,263 and 4,480,109, which are both incorporated by reference in the entirety. Dopamine may be produced, for example, by the methodologies disclosed in U.S. Pat. No. 3,903,077, which is incorporated herein in the entirety. Xamoterol may be produced using any of the methodologies described in U.S. Pat. No. 7,227,028, which is incorporated herein in the entirety. Dobutamine may be produced using any of the methodologies described in U.S. Pat. No. 5,442,120, which is incorporated herein in the entirety.

The above methods may be used to treat any mammal, such as mice or rats for experimental purposes, and even higher mammals, including cats, dogs, cattle, horses and, particularly humans. Dosages must be adjusted, of course, as a function of body weight in accordance with the dosages described above.

Having described the present invention, it will be apparent to one of ordinary skill in the art that many changes and modifications may be made to any of the specific embodiments described above without departing from the spirit and the scope of the claimed invention.

What is claimed is:

1. A method of improving contextual learning in a Down syndrome mammal, which comprises a step of:
administering from about 50 µg to about 800 µg/kg of body weight of a compound (A) selected from the group consisting of L-threo-DOPS, (+)-erythro-DOPS, and a racemic mixture of D- and L-threo-DOPS, and (B) one or more norepinephrine reuptake inhibitor compounds or pharmaceutically-acceptable salts of either compound A or the one or more norepinephrine reuptake inhibitor compounds (B) or both to the mammal in an amount and in a frequency of administration sufficient to improve the contextual learning, wherein the one or more norepinephrine reuptake inhibitor compounds are selected from the group consisting of atomoxetine, mazindol, nisoxetine, reboxetine, viloxazine, (R)-thionisoxetine and clomipramine.

2. The method of claim 1, wherein the improved contextual learning is hippocampally-mediated.

3. The method of claim 1, wherein the norepinephrine reuptake inhibitor compound (B) used is atomoxetine.

4. The method of claim 1, wherein the pharmaceutically-acceptable salts of compound A or the one or more norepinephrine reuptake inhibitors (B) or both are acid addition salts selected from the group consisting of hydrochloride, hydrobromide, hydroiodide, nitrate, sulfate, bisulfate, phosphate, acid phosphate, acetate, lactate, salicylate, isonicotinate, citrate, tartrate, pantothenate, bitartrate, ascorbate, succinate, maleate, gentisinate, fumarate, gluconate, glucanorate, saccharate, formate, benzoate, glutamate, methanesulfonate, ethanesulfonate, benzenesulfonate, p-toluenesulfonic and pamoate.

5. The method of claim 1, wherein the compound A and one or more norepinephrine reuptake inhibitors (B) are administered orally.

6. The method of claim 1, wherein the compound A and one or more norepinephrine reuptake inhibitors (B) are administered parenterally.

7. The method of claim 1, wherein the compound A and one or more norepinephrine reuptake inhibitors (B) are administered subcutaneously.

8. The method of claim 1, which further comprises administering carbidopa with the compound A to the mammal to minimize peripheral CNS effects.

9. The method of claim 1, wherein the mammal is a human.

10. The method of claim 9, wherein the human is an adult.

11. The method of claim 9, wherein the human is an adolescent.

12. The method of claim 9, wherein the human is an infant.

13. The method of claim 9, which improves locus coerulus (LC) function.

14. The method of claim 1, which further comprises after said administering, measuring improvement of contextual learning by standardized test.

15. The method of claim 9, which further comprises after said administering, measuring improvement of contextual learning by standardized test.

16. The method of claim 1, wherein the compound is L-threo-DOPS.

* * * * *